United States Patent
Gatti et al.

(10) Patent No.: US 6,632,799 B2
(45) Date of Patent: *Oct. 14, 2003

(54) INJECTABLE READY-TO-USE SOLUTIONS CONTAINING AN ANTITUMOR ANTHRACYCLINE GLYCOSIDE

(75) Inventors: Gaetano Gatti, Milan (IT); Diego Oldani, Milan (IT); Giuseppe Bottoni, Bergamo (IT); Carlo Confalonier, Milan (IT); Luciano Gambini, Milan (IT); Roberto De Ponti, Milan (IT)

(73) Assignee: Pharmacia & Upjohn Company, Kalamazoo, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/902,030

(22) Filed: Jul. 10, 2001

(65) Prior Publication Data

US 2003/0013666 A1 Jan. 16, 2003

Related U.S. Application Data

(63) Continuation of application No. 09/537,638, filed on Mar. 29, 2000, now abandoned, which is a continuation of application No. 09/149,381, filed on Sep. 8, 1998, now Pat. No. 6,087,340, which is a continuation of application No. 08/368,402, filed on Jan. 3, 1995, now Pat. No. 5,977,082, which is a continuation of application No. 08/224,993, filed on Apr. 8, 1994, now abandoned, which is a continuation of application No. 07/827,938, filed on Jan. 29, 1992, now abandoned, which is a division of application No. 07/471,005, filed on Jan. 25, 1990, now Pat. No. 5,124,318, which is a continuation of application No. 07/341,249, filed on Apr. 20, 1989, now abandoned, which is a continuation of application No. 07/064,653, filed on Jun. 22, 1987, now abandoned, which is a continuation-in-part of application No. 06/878,784, filed on Jun. 26, 1986, now abandoned.

(30) Foreign Application Priority Data

Aug. 2, 1985 (GB) .............................................. 8519452
Dec. 5, 1986 (GB) .............................................. 8629193

(51) Int. Cl.[7] .............................................. A61K 31/70
(52) U.S. Cl. ............................................................. 514/34
(58) Field of Search ................................................ 519/34

(56) References Cited

U.S. PATENT DOCUMENTS

| 4,109,076 A | 8/1978 | Henry et al. |
| 4,296,105 A | 10/1981 | Baurain et al. |
| 4,537,593 A | 8/1985 | Alchas |
| 4,564,054 A | 1/1986 | Gustavsson |
| 4,576,211 A | 3/1986 | Valentini et al. |
| 4,588,403 A | 5/1986 | Weiss et al. |
| 4,786,281 A | 11/1988 | Valentini et al. |

FOREIGN PATENT DOCUMENTS

| CA | 1005760 | 2/1977 |
| CA | 1129344 | 8/1982 |
| CA | 1203482 | 4/1986 |
| DK | 35 36 896 | 4/1986 |
| EP | 401 896 A1 | 12/1990 |
| FR | 2405957 | 5/1979 |
| GB | 2178311 | 2/1987 |

OTHER PUBLICATIONS

*The Interpharm International Dictionary of Biotechnology and Pharmaceutical Manufacturing,* edited By Dean E. Snyder, Publisher Buffalo Grove, IL: Interpharm Press, Inc., 1992.
Merck Index, 10th edition, 1983, p. 499, Entry No. 3435.
Bosanquet, "Stability of solutions of antineoplastic agents during preparation and storage for in vitro assays", *Cancer Chemotherapy and Pharmacology,* vol. 17, 1986, pp. 1–10.
Rolf Kaltofen, Joachim Ziemann et al., Tabellenbuch Chemie, 12th edition, pp. 172, 181.
Yüksel, "Determination of Ceftriaxone in Aqueous Humour and Serum Samples by Differrential–pulse Adsorptive Stripping Voltammetry", *Analyst,* vol. 119, 1994, pp. 1575–1577.
Falbe et al., *Rompp Chemie Lexikon,* 9th edition, Georg Thieme Verlag Stuttgart, New York, 1992, "Buffers", pp. 3677–3678.
Mortimer, *Chemie,* 3rd edition, Georg Thieme Verlag Stuttgart, New York, 1980, pp. 490–494.
Europaischez Arzneibuch, vol. III, 1979, p. 654 (English translation provided.).
Arcamone et al. (1972), "Structure and Physiochemical Properties of Adriamycin (Doxorubicin)," International Symposium on Adriamycin, Springer–Verlag, Berlin, pp. 9–22.
Beijnen, J.H. et al. (1985), "Aspects of the Chemical Stability of Doxorubicin and Seven Other Anthracyclines in Acidic Solution," *Pharmaceutisch Weekblad Scientific Edition,* vol. 7, pp. 109–116.
German Patent Office Decision dated Oct. 8, 1996 (English translation attached) revoking Patent No. 3621844.
Wang and Kowal (1980), "Review of Excipients and pH's for Parenteral Products Used in the United States," *J. of the Parenteral Drug Association,* vol. 14, p. 452–462.
Harris, Daniel C. (1995), "Quantitative Chemical Analysis," 4th Edition, W.H. Freeman and Company.
Topics in Antibiotic Chemistry, 2, 109–115, 1978.
Arcamone et al. (1969, "Adrimycin, 14–Hydroxydaunomycin, a New Antitumor Antibiotic from *S. Peucetius Var. Caesius,*" Biotechnology and Bioengineering, vol. XI, pp. 1101–1110.

(List continued on next page.)

*Primary Examiner*—Elli Peselev
(74) *Attorney, Agent, or Firm*—McDonnell Boehnen Hulbert & Berghoff

(57) ABSTRACT

A sealed glass container containing therein a stable, injectable, sterile, pyrogen-free doxorubicin anti-tumor composition in a solution which consists essentially of a physiologically acceptable salt of doxorubicin dissolved in a physiologically acceptable solvent therefor, wherein said solution has not been reconstituted from a lyophilizate, and wherein said solution has a pH of from 2.5–3.5 and a concentration of said doxorubicin of from 0.1 to 100 mg/ml.

17 Claims, 6 Drawing Sheets

OTHER PUBLICATIONS

Despois et al. (1967), "Isolement D'un Nouvel Antibiotique Doue D'Activite Antitumorale: La Rubidomycine (13.057 R.P.) Identite De La Rubidomycine et de La Daunomycine," Path. Biol., vol. 15, pp. 887–891.

Lokich et al. (1983), "constant Infusion Schedule for Adrimycin: A Phase I–II Clinical Trial of a 30–Day Schedule by Ambulatory Pump Delivery System," J. Clinical Oncology, vol. 1, pp. 24–28.

Wasserman and Bundgaard (1983), "Kinetics of the Acid–Catalyzed Hydrolysis of Doxorubicin," International J. Pharmaceutics, vol. 14, pp. 73–78.

Merck Index (1996), Mitoxantrone, $12^{th}$ Edition, Entry 6303, p. 1064.

Martindale (1989), Mitotone, The Pharmaceutical Press, $29^{th}$ Edition, London, Entry 1852-x, pp. 643–645.

ABPI Data Sheet Compendium, 1994–1995, "Novantron Injection," Lederle Laboratories, pp. 752–754.

Geigy Scientific Tables, vol. 3, Physical Chemistry Composition of Blood Hematology Somatometric Data $8^{th}$ revised and enlarged edition, Edited by C. Lentner, pp. 54–60.

Dorr (1979), "Incompatibilities with Parenteral Anticancer Drugs," The American Journal of Intravenous Therapy, Feb./Mar. pp. 42, 45–46, 52.

Bernard, J., et al. (1969) Rubidomycin, Springer–Verlag, Berlin–Heidelberg–New York.

Karlsen, J., et al (1983), "Stability of Cytotoxic Intravenous Solutions Subjected to Freeze–Thaw Treatment," Nor Pharm ACTA, vol. 45, pp. 61–67.

Vogelzang, N.J., et al. (1985), "Phase I Trial of an Implanted Battery–Powered Programmable Drug Delivery System for Continuous Doxorubicin Adminstration," Journal of Clinical Oncology, vol. 3, No. 3 (Mar.), pp. 407–414.

Beijnen et al. (1985), "Stability of Anthracycline Antitumor Agents in Infusion Fluids," J. Parenteral Science and Technology, vol. 39, pp. 220–222.

The Merck Index (1983), "Doxorubicin," $10^{th}$ Edition, AN–3435, p. 499.

Kano et al., Electrochemical Properties of Adriamycin Adsorbed on a Mercury Electrode Surface, The Chemical Society of Japan, Bull. Chem. Soc. Jpn., 57, 2383–2390 (1984).

Kano et al., The Effects of the pH and the Temperature on the Oxidation–reduction Properties of Adriamycin Adsorbed on a Mercury Electrode Surface, The Chemical Society of Japan, Bull. Chem. Soc. Jpn., 58, 424–428 (1985).

Tan, C. et al., Daunomycin, an Anti–Tumor Antibiotic, in the Treatment of Neoplastic Disease, Mar. 1967, Cancer 20:333–353.

Samuels, L.D. et al., "Daunorubicin Therapy in Advanced Neuroblastoma", Apr. 1971, Cancer 27:831–834.

Miller, A.A. and Schmidt, C.G., "Clinical Pharmacology and Toxocology of 4" –O–Tetrahydropyranyladriamycin, Mar. 1, 1987, Cancer Research 47:1461–1465.

Holton, C.P. et al. "Clinical Study of Daunomycin and Prednisone for Induction of Remission in Children with Advanced Lukemia", New England Journal of Medicine, Jan. 23, 1969, 208:171–174.

Rozencweig, M. et al., "Preliminary Experience with Marcellomycin: Pre–Clinical and Clinical Aspects" p. 549–561.

Bradner and Misiek, (1977) The Journal of Antibiotics, "Bohemic Acid Complex. Biological Characterization of the Antibiotics, Musettamycin and Marcellomycin," 30(6) 519–522.

Kjeld Ilver, Almen Galenisk Farmaci—Forelæsningsnoter, Dansk Farmaceutforenings Forlag 1971, pp. 132–136. (English translation provided).

Gjelstrup et al. (1983), Almen Farmaaci I, Dansk Farmacetuforenings Forlag, København, pp. 404–408, 440, 442–443, 447, 451. (English translation provided).

Erik Sandell, (1967), Galenisk Farmaci, $2^{nd}$ edition, Stockholm, pp. 214. (English translation provided).

Erik Sandell, (1982), Galenisk Farmaci, $3^{rd}$ edition, Stockholm, pp. 123. (English translation provided).

Svend Aage Schou & V. Gaunø Jensen (1959), Træk af den flaeniske farmaci, Store Nordiske Videnskabsboghandel, pp. 220. (English translation provided).

Arcamone, F. (1977), Lloydia, "New Antitumor Anthracyclines," 40(1):45–66.

Naff et al., (1982) Anthracycline Antibiotics, Antharacyclines in the National Cancer Institute Program, Hassan S. El Khadham, editor, Academic Press, pp. 1–57.

Formularium Der Nederlandse Apothekers, (1983) pp. I.8, I.24, I.63.

Formularium Der Nederlandse Apothekers, (1979) pp. I.64, I.82.

Formularium Der Nederlandse Apothekers, (1985) pp. I.64a.

Formularium Der Nederlandse Apothekers, (1989) pp. I.88.

Formularium Der Nederlandse Apothekers, (1992) pp. 1.63.a.

Bohme and Harke (1979), Europäisches Arzneibuch,Band III, Kommentar, Wissenschaftliche Verlagsgesellschaft mbH Stuttgart, pp. 654 (English Translation provided.).

Arcamone et al. (1972), "Structure and Physicochemical Properties of Adriamycin (Doxorubicin)," International Symposium on Adriamycin, pp. 9–22.

Harris, Quantitative Chemical Analysis, Fourth Edition, W.H. Freeman & Company, New York, pp. 240.

Bernard et al., editors (1969), Rubidomycin A New Agent Against Cancer, pp. ix–181.

Karlsen et al. (1983), "Stability of cytotoxic intravenous solutions subjected to freeze–thaw treatment," Nor. Pharm. Acta, 45, 61–67.

Falck, K., et al. (1979), "Mutagenicity in Urine of Nurses Handling Cytostatic Drugs", The Lancet, Jun. 9, 1979, p. 1250–1251.

"Union Warns of Cancer Drug Dangers", Chemistry and Industry, Jul. 4, 1983.

Lassila, O., et al. (1980), "Immune Function in Nurses Handling cytostatic Drugs", The Lancet, Aug. 30, 1980., p. 482.

Abstract of Medical Economics Co., Chemistry–Industry, Feb. 7, 1983, p. 99.

Chemical Abstract, vol. 99, p. 345 (1983), Abst. No. 99:218014y.

INJECTABLE READY-TO-USE SOLUTIONS CONTAINING AN ANTITUMOR ANTHRACYCLINE GLYCOSIDE

This is a continuation of U.S. Ser. No. 09/537,638, filed Mar. 29, 2000, now abandoned, which is a continuation of U.S. Ser. No. 09/149,381, filed Sep. 8, 1998, now U.S. Pat. No. 6,087,340, which is a continuation of U.S. Ser. No. 08/368,402, filed Jan. 3, 1995, now U.S. Pat. No. 5,977,082, which is a continuation of U.S. Ser. No. 08/224,993, filed Apr. 8, 1994, now abandoned, which is a continuation of U.S. Ser. No. 07/827,938, filed Jan. 29, 1992, now abandoned, which is a divisional of U.S. Ser. No. 07/471,005, filed Jan. 25, 1990, now U.S. Pat. No. 5,124,318, which is a continuation of U.S. Ser. No. 07/341,249, filed Apr. 20, 1989, now abandoned, which is a continuation of U.S. Ser. No. 07/064,653, filed Jun. 22, 1987, now abandoned, which is a continuation-in-part of U.S. Ser. No. 06/878,784, filed Jun. 26, 1986, now abandoned.

BACKGROUND OF THE INVENTION

1. Field of the Invention

The present invention relates to a stable, injectable, ready-to-use solution of an antitumor anthracycline glycoside, e.g. doxorubicin (Adriamycin®), to a process for preparing such a solution, and providing the same in a sealed container, and to a method for treating tumors by the use of the ready-to-use solution.

2. Description of the Related Art

The anthracycline glycoside compounds are a well known class of compounds in the antineoplastic group of agents, of which doxorubicin is a typical, and the most widely used, representative: Doxorubicin. Anticancer Antibiotics, Federico Arcamone, 1981, Publ: Academic Press, New York, N.Y.; Adriamycin Review, EROTC International Symposium, Brussels, May, 1974, edited by M. Staquet, Publ. Eur. Press Medikon, Ghent, Belg.; Results of Adriamycin Therapy, Adriamycin Symposium at Frankfurt/Main 1974 edited by M. Ghione, J. Fetzer and H. Maier, publ.: Springer, New York, N.Y.

In the past, solutions of anthracycline glycosides have been prepared and the stability thereof has been studied. However, results of these studies have been inconsistent, and no clear parameters have emerged for maintenance of a stable anthracycline glycoside, e.g., doxorubicin, solution. Bosanquet, in a recent article entitled "Stability of solutions of antineoplastic agents during preparation and storage for in vitro assays," (Cancer Chemother. Pharmacol. 1986, 17, 1–10) reviews the field of stability studies, with particular emphasis on doxorubicin (Adriamycin®). He points out that "very little can be categorically stated about the stability of adriamycin, and a very carefully designed study is urgently required to resolve these conflicting results."

At present, anthracycline glycoside antitumor drugs, in particular, e.g., doxorubicin, are solely available in the form of lyophilized preparations, which need to be reconstituted before administration.

Both the manufacturing and the reconstitution of such preparations expose the involved personnel (workers, pharmacists, medical personnel, nurses) to risks of contamination which are particularly serious due to the toxicity of the antitumor substances.

Indeed, the Martindale Extra Pharmacopoeia 28th edition, page 175 left column, reports on adverse effects of antineoplastic drugs and recommends that "They must be handled with great care and contact with skin and eyes avoided; they should not be inhaled. Care must be taken to avoid extravasation since pain and tissue damage may ensue".

Similarly, Scand. J. Work Environ Health vol. 10(2), pages 71–74 (1984), as well as articles in Chemistry Industry, Issue Jul. 4, 1983, page 488, and Drug-Topics-Medical-Economics-Co, Issue Feb. 7, 1983, page 99, report severe adverse effects observed in medical personnel exposed to use of cytostatic agents, including doxorubicin.

Even though the effect of long-term low-level exposure to such cytotoxic drugs is not yet completely known, there is certainly a hazard for those who regularly prepared and administer these substances in view of the fact that they are known mutagens and carcinogens in animals and implicated as carcinogens in man.

To administer a lyophilized preparation, double handling of the drug is required, the lyophilized cake having to be first reconstituted and then administered. Moreover, in some cases, the complete dissolution of the powder may require prolonged shaking because of solubilization problems. Reconstitution of a lyophilized cake or powder can result in formation of aerosol droplets which can be inhaled or can come into contact with skin or mucous membranes of those handling the solution.

SUMMARY OF THE INVENTION

As the risks connected with the manufacturing and the reconstitution of a lyophilized preparation would be highly reduced if a ready-to-use solution of the drug were available, the present inventors have developed a stable, therapeutically acceptable injectable solution of an anthracycline glycoside drug, e.g. doxorubicin, whose preparation and administration does not require either lyophilization or reconstitution.

According to the present invention, there is provided a stable, injectable, sterile, pyrogen-free, anthracycline glycoside solution which consists essentially of a physiologically acceptable salt of an anthracycline glycoside dissolved in a physiologically acceptable solvent therefor, which has not been reconstituted from a lyophilizate, which has a pH of from 2.5 to 3.5 and which is preferably contained in a sealed glass container.

DETAILED DESCRIPTION OF THE PREFERRED EMBODIMENTS

Figure 1:
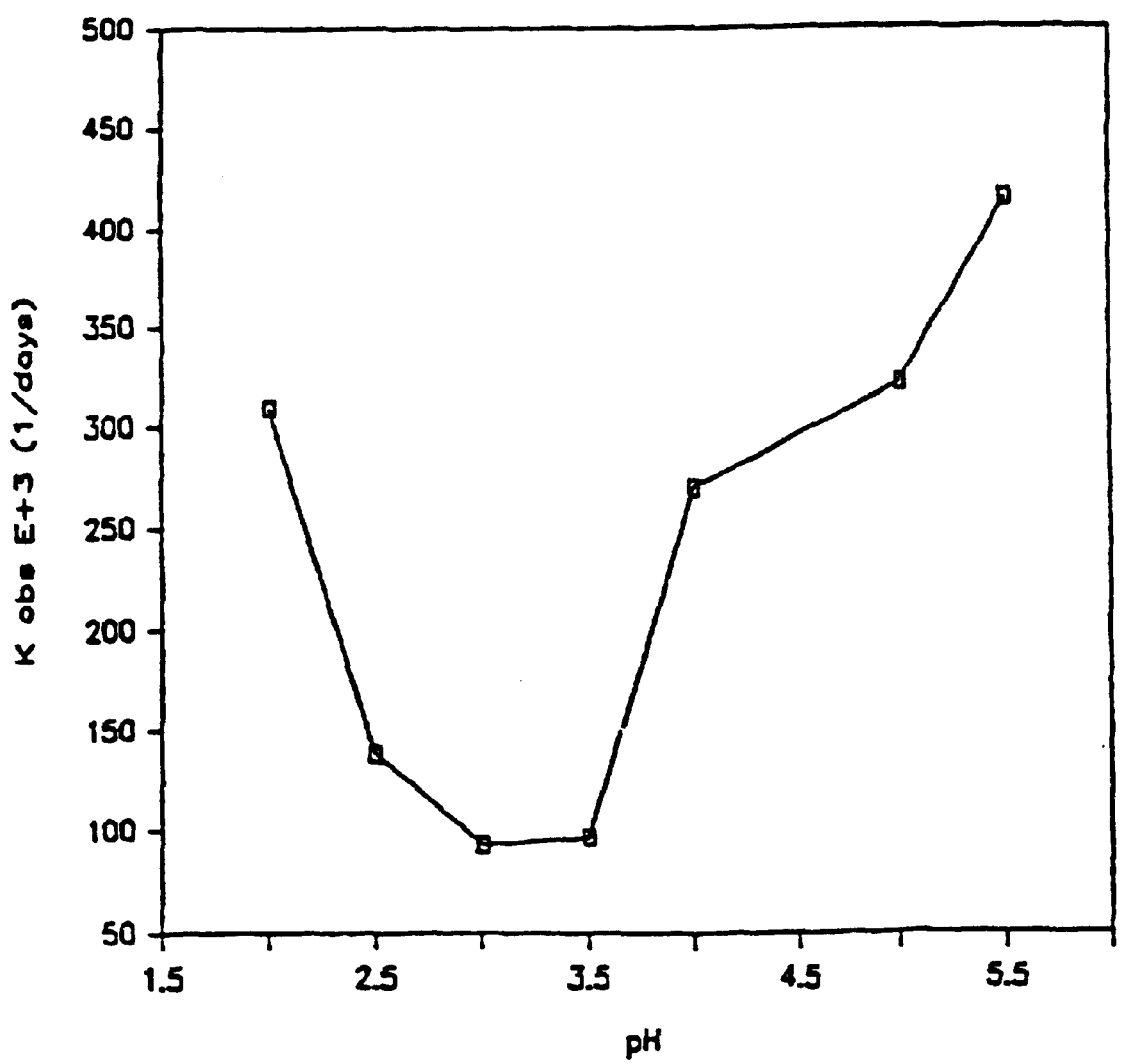
FIG. 1 is a $K_{obs}$ pH profile for doxorubicin.HCl degradation at 55° C. in sterile water.

A preferred pH range for the anthracycline glycoside solution of this invention is from 2.5 to 3.5. A more preferred range is from 2.7 to 3.5, and a particularly preferred range is from 2.7 to 3.3. A range of 2.7 up to about 3.0 may also be mentioned as a useful range.

The preferred anthracycline glycoside is doxorubicin hydrochloride. It is known that doxorubicin hydrochloride is more stable in acidic than neutral or basic solutions. See Analytical Profiles of Drug Substances, Vol. 9, Klaus Florey, ed. (Academic Press 1980). A number of stability studies are summarized in Bosanquet, Cancer Chemother. Pharrnacol. 17, 1986, 1–10. However, these studies are inconsistent, in part because of the varying media used to make up the solutions and the methods used to measure stability. Taken as a whole, the prior art has not appreciated with any degree of certainty how to prepare a stable, injectable doxorubicin solution, as a function of pH.

Martindale-The Extra Pharmacopeia 28th edition, 1828, on page 205, indicates that a 0.5% solution of doxorubicin hydrochloride and water has a pH of 3.8 to 6.5. Reconstitution of the commercial freeze dried formulation which is made of doxorubicin hydrochloride and lactose, leads to a solution having a pH in the range of between 4.5 and 6, containing doxorubicin at 2 milligrams per milliliter concentration and lactose, and additionally containing sodium chloride when saline is used for reconstitution. In order to lower the pH below that of reconstituted solutions, one must add an acid to lower the pH. In the past there was little motivation for a user of the drug to add an acid to lower the pH, since it was not recognized that the drug was actually more stable at pH's between about 2.5 and 3.5. According to the present invention, it has been discovered that anthracycline glycosides, such as doxorubicin hydrochloride, are stable in the pH range disclosed herein in physiologically acceptable media. The prior art did not recognize stability for an injectable doxorubicin solution in the particular narrow pH range disclosed herein, so this pH range was not considered to be a particularly useful range for administration of this drug.

Preferably the solution of the invention is provided in a sealed container, especially one made of glass, either in a unit dosage form or in a multiple dosage form.

In addition to doxorubicin, other anthracycline glycosides include 4'-epi-doxorubicin (i.e. epirubicin), 4'-desoxy-doxorubicin (i.e. esorubicin), 4'-desoxy-4'-iodo-doxorubicin, daunorubicin and 4-demethoxydaunorubicin (i.e. idarubicin).

Any physiologically acceptable salt of the anthracycline glycoside may be used for preparing the solution of the invention. Examples of suitable salts may be, for instance, the salts with mineral inorganic acids such as hydrochloric, hydrobromic, sulfuric, phosphoric, nitric and the like, and the salts with certain organic acids such as acetic, succinic, tartaric, ascorbic, citric, glutamic, benzoic, methanesulfonic, ethanesulfonic and the like. The salt with hydrochloric acid is a particularly preferred salt, especially when the anthracycline glycoside is doxorubicin.

Any solvent which is physiologically acceptable and which is able to dissolve the anthracycline glycoside salt may be used. The solution of the invention may also contain one or more additional components such as a co-solubilizing agent (which may be the same as a solvent), a tonicity adjustment agent, a stabilizing agent and a preservative. Examples of solvents, co-solubilizing agents, tonicity adjustment agents, stabilizing agents and preservatives which can be used for the preparation of the anthracycline glycoside solutions of the invention are hereunder reported.

Suitable solvents and co-solubilizing agents may be, for instance, water; physiological saline; aliphatic amides, e.g. N,N-dimethylacetamide, N-hydroxy-2-ethyl-lactamide and the like; alcohols, e.g. ethanol, benzyl alcohol and the like; glycols and polyalcohols, e.g. propyleneglycol, glycerin and the like; esters of polyalcohols, e.g. diacetine, triacetine and the like; polyglycols and polyethers, e.g. polyethyleneglycol 400, propyleneglycol methylethers and the like; dioxolanes, e.g. isopropylidenglycerin and the like; dimethylisosorbide; pyrrolidone derivatives, e.g. 2-pyrrolidone, N-methyl-2-pyrrolidone, polyvinylpyrrolidone (co-solubilizing agent only) and the like; polyoxyethylenated fatty alcohols, e.g., Brij® and the like; esters of polyoxyethylenated fatty acids, e.g., Cremophor®, Myrj® and the like; polysorbates, e.g., Tweens®, polyoxyethylene derivatives of polypropyleneglycols, e.g., Pluronics®.

A particularly preferred co-solubilizing agent is polyvinylpyrrolidone.

Suitable tonicity adjustment agents may be, for instance, physiologically acceptable inorganic chlorides, e.g. sodium chloride; dextrose; lactose; mannitol; sorbitol and the like.

Preservatives suitable for physiological administration may be, for instance, esters of parahydroxybenzoic acid (e.g., methyl, ethyl, propyl and butyl esters, or mixtures of them), chlorocresol and the like.

Suitable stabilizing agents include monosaccharides (e.g., galactose, fructose, and fucose), disaccharides (e.g., lactose), polysaccharides (e.g., dextran), cyclic oligosaccharides (e.g., α-, β-, γ-cyclodextrin), aliphatic polyols (e.g., mannitol, sorbitol, and thioglycerol), cyclic polyols (e.g. inositol) and organic solvents (e.g., ethyl alcohol and glycerol). These may be included in concentrations of from about 0.25–10% w/v, preferably 0.5–5% w/v in the solution.

The above mentioned solvents and co-solubilizing agents, tonicity adjustment agents, stabilizing agents and preservatives can be used alone or as a mixture of two or more of them.

Examples of preferred solvents are water, ethanol, polyethylene glycol and dimethylacetamide as well as mixtures in various proportions of these solvents. Water is a particularly preferred solvent. Other solvents giving good results in terms of stability are 0.9% sodium chloride solution (i.e., physiological saline), and, especially, 5% dextrose solution, 5% mannitol solution and 5% sorbitol solution, i.e., aqueous solutions containing approximately 5% of, respectively, dextrose, mannitol or sorbitol. Small variations (±2–3%) of these additional ingredients also fall within the scope of the present invention.

To adjust the pH within the range of from 2.5 to about 3.5, a physiologically acceptable acid is added to the solution of the anthracycline glycoside. The acid should be a physiologically acceptable acid, e.g., an inorganic mineral acid such as hydrochloric, hydrobromic, sulfuric, phosphoric, nitric and the like, or an organic acid such as acetic, succinic, tartaric, ascorbic, citric, glutamic, benzoic, methanesulphonic, ethanesulfonic and the like, or also an acidic physiologically acceptable buffer solution, e.g., a chloride buffer, an acetate buffer, a phosphate buffer and the like.

In the solutions of the invention the concentration of the anthracycline glycoside may vary within broad ranges, preferably from 0.1 mg/ml to 100 mg/ml, in particular from 0.1 mg/ml to 50 mg/ml, most preferably from 1 mg/ml to 20 mg/ml.

The preferred ranges of concentration may be slightly different for different anthracycline glycosides. Thus, for example, preferred concentrations for doxorubicin are from about 2 mg/ml to about 50 mg/ml, preferably from 2 mg/ml to 20 mg/ml, particularly appropriate values being 2 mg/ml and 5 mg/ml. Similar concentrations are preferred also for 4'-epi-doxorubicin, 4'-desoxy-doxorubicin and 4'-desoxy-4'-iodo-doxorubicin. Preferred ranges of concentration for daunorubicin and 4-demethoxy-daunorubicin are from 0.1 mg/ml to 50 mg/ml, preferably from 1 mg/ml to 20 mg/ml, concentrations of 1 mg/ml and 5 mg/ml being particularly appropriate.

Suitable packaging for the anthracycline glycoside solutions may be all approved containers intended for parenteral use, such as plastic and glass containers, ready-to-use syringes and the like. Preferably the container is a sealed glass container, e.g. a vial or an ampoule. A hermetically sealed glass vial is particularly preferred.

According to a particularly preferred feature of the invention, there is provided, in a sealed glass container, a sterile, pyrogen-free, injectable doxorubicin solution which consists essentially of a physiologically acceptable salt of doxorubicin dissolved in a physiologically acceptable solvent therefor, which has not been reconstituted from a lyophilizate and which has a pH of from 2.5 to 3.5.

In the above indicated preferred feature of the invention the physiologically acceptable salt of doxorubicin may be, e.g. the salt with a mineral inorganic acid such as hydrochloric, hydrobromic, sulfuric, phosphoric, nitric and the like, or the salt with an organic acid such as acetic, succinic, tartaric, ascorbic, citric, glutamic, benzoic, methanesulfonic, ethanesulfonic and the like. The hydrochloride salt is a particularly preferred salt.

For the solution hereabove indicated as a preferred feature of the invention suitable solvents, co-solubilizing agents, tonicity adjustment agents, stabilizing agents and preservatives may be the same as those previously recited in this specification. Water is a particularly preferred solvent.

Also, the physiologically acceptable acid which is added to adjust the pH to from 2.5 to about 3.5 may be one of those previously specified. When it is desired to adjust the pH of the above said preferred solution to a value of from 2.5 to about 3.5, hydrochloric acid is an especially preferred acid. Preferred pH values for the above said preferred solutions of the invention are from about 2.7 to about 3.3.

Though the concentration of doxorubicin in the above preferred feature may vary within the broad range from 0.1 mg/ml to 100 mg/ml, preferred concentrations are from 2 mg/ml to 50 mg/ml, most preferably from 2 mg/ml to 20 mg/ml: examples of especially preferred concentrations of doxorubicin are 2 mg/ml and 5 mg/ml.

The invention also provides a process for producing a sterile, pyrogen-free anthracycline glycoside solution with a pH of from 2.5 to 3.5 which process comprises dissolving a physiologically acceptable salt of the anthracycline glycoside, which salt is not in the form of a lyophilizate, in a physiologically acceptable solvent therefor; adding a physiologically acceptable acid or buffer to adjust the pH within the said range as desired; and passing the resulting solution through a sterilizing filter.

One or more additional components such as co-solubilizing agents, tonicity adjustment agents, stabilizing agents and preservatives, for instance of the kind previously specified, may be added to the solution prior to passing the solution through the sterilizing filter.

With the solutions of the invention it is possible to obtain compositions having a very high concentration of the anthracycline glycoside active substance even at 50 mg/ml and more. This constitutes a great advantage over the presently available lyophilized preparations wherein high concentrations of anthracycline glycoside can only be obtained with difficulty because of solubilization problems encountered in reconstitution, mainly with saline. The presence of the excipient, e.g. lactose, in the lyophilized cake, and its generally high proportion in respect of the active substance, even up to 5 parts of excipient per part of active substance, has a negative effect on solubilization so that difficulties may arise in obtaining dissolution of the lyophilized cake, especially for concentrations of anthracycline glycoside higher than 2 mg/ml.

The solution of the invention are characterized by a good stability. Solutions in various solvents and with different pH's and concentrations have been found to be stable for long periods at temperatures accepted for the storage of pharmaceutical preparations. This is illustrated in the Examples which follow.

Due to the well known anti-tumor activity of the anthracycline glycoside active drug substance, the pharmaceutical compositions of the invention are useful for treating tumors in both human and animal hosts. Examples of tumors that can be treated are, for instance, sarcomas, including osteogenic and soft tissue sarcomas, carcinomas, e.g., breast-, lung-, bladder-, thyroid-, prostate- and ovarian carcinoma, lymphomas, including Hodgkin and non-Hodgkin lymphomas, neuroblastoma, melanoma, myeloma, Wilms tumor, and leukemias, including acute lymphoblastic leukemia and acute myeloblastic leukemia. See Kirk-Othmer's Encyclopedia of Chemical Technology, Volume 5, pages 478–479 (1979).

Examples of specific tumors that can be treated are Moloney Sarcoma Virus, Sarcoma 180 Ascites, solid Sarcoma 180, gross transplantable leukemia, L 1210 leukemia and lymphocytic P 388 leukemia.

Thus, according to the invention there is also provided a method of inhibiting the growth of a tumor, in particular one of those indicated above, which comprises administering to a host suffering from said tumor an injectable solution according to the invention containing the active drug substance in an amount sufficient to inhibit the growth of said tumor.

The injectable solutions of the invention are administered by rapid intravenous injection or infusion according to a variety of possible dose schedules. A suitable dose schedule for doxorubicin may be, for example, of 60 to 75 mg of active drug substance per $m^2$ of body surface given as a single rapid infusion and repeated at 21 days; an alternative schedule may be of 30 mg/$m^2$ per day by intravenous route for 3 days, every 28 days. Suitable dosages for 4'-epi-doxorubicin and 4'-desoxy-doxorubicin may be, for instance, of 75 to 90 mg/$m^2$ given in a single infusion to be repeated at 21 days, and similar dosages may be useful also for 4'-desoxy-4'-iodo-doxorubicin.

Idarubicin, i.e. 4-demethoxy-daunorubicin, may be administered intravenously at a single dose of 13–15 mg/$m^2$ every 21 days in the treatment of solid tumors, while in the treatment of leukemias a preferred dose schedule is, e.g., of 10–12 mg/$m^2$ day be intravenous route for 3 days, to be repeated every 15–21 days; similar dosages may be followed also for daunorubicin.

EXAMPLES

The invention now being generally described, the same will be better understood by reference to certain specific examples which are included herein for purposes of illustration only and are not intended to be limiting of the invention or any embodiment thereof, unless specified.

With reference to the first three examples, the stability controls on the ready-to-use solutions were carried out by means of high performance liquid chromatography (HPLC), at the following experimental conditions:

Liquid chromatograph: Varian model 5010

Spectrophotometric detector: Knauer model 8700

Integrating recorder: Varian model CDS 401

Injection valve: Rheodyne model 7125 fitted with a 10 mcl sample loop

Chromatographic column: Waters .mu.-Bondapak C18 (length=300 mm; inner diameter=3.9 mm; average particle size=10 mcm)

Column temperature: ambient (about 22° C.±2° C.)

Mobile phase: water:acetonitrile (69:31 v/v) adjusted to pH 2 with phosphoric acid, filtered (sintered glass filter, 1 mcm or finer porosity) and deaerated Mobile phase flow rate: 1.5 ml/min Analytical wavelength: 254±1 nm
Integrating recorder sensitivity: 512
Chart speed: 1 cm/min The stability data obtained, using high performance liquid chromatography (HPLC) for the determination of potency, are reported in the following Table 1:

TABLE 1

INITIAL VALUES
Concentration: 1.994 mg/ml
Relative % Assay: 100.0                pH = 5.2

| TIME (weeks) | 4° C. Conc. mg/ml | 4° C. Rel. % Assay | 35° C. Conc. mg/ml | 35° C. Rel. % Assay | 45° C. Conc. mg/ml | 45° C. Rel. % Assay | 55° C. Conc. mg/ml | 55° C. Rel. % Assay |
|---|---|---|---|---|---|---|---|---|
| 1 | 1.992 | 99.9 | 1.917 | 96.1 | 1.768 | 88.7 | 1.493 | 75.0 |
| 2 |  |  | 1.843 | 92.4 | 1.618 | 81.1 | 1.166 | 58.5 |
| 3 |  |  | 1.774 | 89.0 | 1.506 | 75.5 | 0.830 | 41.6 |
| 4 | 1.974 | 99.0 | 1.720 | 86.3 | 1.393 | 69.9 |  |  |
| 12 | 1.980 | 99.3 |  |  |  |  |  |  |

$t_{90}$ (days) extrapolated according to Arrhenius equation:
$t_{90}$ at 4° C. = 815 days
$t_{90}$ at 8° C. = 480 days At these conditions, the peak of the anthracycline glycoside showed a retention time of about 6 minutes.

The obtained results are reported in Tables accompanying Examples 1–3.

The extrapolation of the analytical data in order to determine the time when the 90% of the initial assay could be expected ($t_{90}$ value) was made following an Arrhenius plot.

This procedure of analytical data treatment is well known and widely used and described in the art: see e.g., Chemical Stability of Pharmaceuticals, Kennet A. Connors, Gordon L. Amidon, Lloyd Kennon, Publ. John Wiley and Sons, New York, N.Y., 1979.

The term "teflon" recurring in the examples refers to "Teflon™".

Example 1

| Composition | for 80 vials | (for 1 vial) |
|---|---|---|
| Doxorubicin·HCl | 0.8 g | (10 mg) |
| Water for injections q.s. to | 0.4 l | (5 ml) |

Doxorubicin.HCl (0.80 g) was dissolved in 90 percent of the amount of water for injections, de-aerated by nitrogen bubbling. The pH of the solution was not adjusted. Further de-aerated water for injections was then added to bring the solution to its final volume (0.40 l).

The solution was filtered through a 0.22 μm microporous membrane under nitrogen pressure. Volumes of 5 ml of the solution were distributed into type I-colorless glass vials having 5/7 ml capacity. The vials were then closed with chlorobutyl teflon-faced rubber stoppers and sealed with aluminum caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 12 weeks (4° C.).

Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

Example 2

| Composition | for 80 vials | (for 1 vial) |
|---|---|---|
| Doxorubicin·HCl | 0.8 g | (10 mg) |
| Hydrochloric acid 0.1 N q.s. to | pH = 3 | (pH = 3) |
| Water for injections q.s. to | 0.4 l | (5 ml) |

Doxorubicin.HCl (0.8 g) was dissolved in 90 percent of the amount of water for injections, de-aerated by nitrogen bubbling. The hydrochloric acid was then added dropwise to adjust the pH of the solution to 3. Further de-aerated water for injections was then added to bring the solution to its final volume (0.4 l).

The solution was filtered through a 0.22 μm microporous membrane under nitrogen pressure. Volumes of 5 ml of the solution were distributed into type I-colorless glass vials having 5/7 ml capacity. The vials were then closed with chlorobutyl teflon-faced rubber stoppers and sealed with aluminum caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 12 weeks (4° C.).

The stability data obtained, using high performance liquid chromatography (HPLC) for the determination of potency, are reported in the following Table 2:

TABLE 2

INITIAL VALUES  
Concentration: 1.992 mg/ml  
Relative % Assay: 100.0          pH = 3.0

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 1.995 | 100.2 | 1.952 | 98.0 | 1.919 | 96.3 | 1.493 | 75.0 |
| 2 | | | 1.889 | 94.8 | 1.851 | 92.9 | 1.036 | 51.9 |
| 3 | | | 1.876 | 94.2 | 1.565 | 78.6 | 0.730 | 36.7 |
| 4 | 1.979 | 99.4 | 1.808 | 90.8 | 1.393 | 69.9 | | |
| 12 | 1.972 | 99.0 | | | | | | |

$t_{90}$ (days) extrapolated according to Arrhenius equation:  
$t_{90}$ at 4° C. = 3970 days  
$t_{90}$ at 8° C. = 2000 days Similar stability data can be observed also for analogous solutions containing either doxorubicin hydrochloride at 5 mg/ml concentration, or 4'-epi-doxorubicin, 4'-desoxy-doxorubicin, 4'-desoxy-4'-iodo-doxorubicin, daunorubicin or 4-demethoxy-daunorubicin, as hydrochloride salts, at both 2 mg/ml and 5 mg/ml concentration.

Example 3

| Composition | for 80 vials | (for 1 vial) |
|---|---|---|
| Doxorubicin·HCl | 0.8 g | (10 mg) |
| Hydrochloric acid 0.1 N q.s. to | pH = 3 | (pH = 3) |
| Water for injections q.s. to | 0.4 l | (5 ml) |

Doxorubicin.HCl (8.0 g) was dissolved in 90 percent of the amount of water for injections, de-aerated by nitrogen bubbling. The hydrochloric acid was then added dropwise to adjust the pH of the solution 3. Further de-aerated water for injections was then added to bring the solution to its final volume (0.4 l).

The solution was filtered through a 0.22 μm microporous membrane under nitrogen pressure. Volumes of 5 ml of the solution were distributed into type I-colorless glass vials having 5/7 ml capacity. The vials were then closed with chlorobutyl teflon-faced rubber stoppers and sealed with aluminum caps.

The stability of the solutions in the vials was tested. The vials were stored at temperatures of 55° C., 45° C. and 35° C. (accelerated stability controls) and at 4° C. for up to 3 weeks (55° C.), 4 weeks (45° C. and 35° C.) and 12 weeks (4° C.).

The stability data obtained, using high performance liquid chromatography (HPLC) for the determination of potency, are reported in the following Table 3:

TABLE 3

INITIAL VALUES  
Concentration: 20.06 mg/ml  
Relative % Assay: 100.0          pH = 2.95

| | TEMPERATURE | | | | | | | |
|---|---|---|---|---|---|---|---|---|
| | 4° C. | | 35° C. | | 45° C. | | 55° C. | |
| TIME (weeks) | Conc. mg/ml | Rel. % Assay | Conc. mg/ml | Rel. % Assay | Conc. mg/ml | Rel. % Assay | Conc. mg/ml | Rel. % Assay |
| 1 | 20.06 | 100.0 | 19.56 | 97.5 | 17.84 | 88.9 | 12.31 | 61.4 |
| 2 | | | 18.87 | 94.1 | 15.61 | 77.8 | 7.09 | 35.3 |
| 3 | | | 18.24 | 90.9 | 13.41 | 66.8 | 3.13 | 15.6 |
| 4 | 19.91 | 99.2 | 17.51 | 87.3 | 11.07 | 55.2 | | |
| 12 | 19.80 | 98.7 | | | | | | |

$t_{90}$ (days) extrapolated according to Arrhenius equation:  
$t_{90}$ at 4° C. = 3700 days  
$t_{90}$ at 8° C. = 1780 days Similar stability data can be observed for analogous solutions containing 4'-epi-doxorubicin or 4'-desoxy-doxorubicin, as hydrochloride salts, at the same 20 mg/ml concentration.

The following examples regarding stability profile and shelf-life forecasts were carried out under accelerated temperature conditions on 5.0 ml of 2 mg/ml doxorubicin.HCl solutions in a container-closure system consisting of: glass type I, 8 ml top capacity vial; teflon-faced chlorobutyl rubber bung; aluminum seal.

pH-Stability Profile at 55° C. of Doxorubicin.HCl Solutions in Sterile Water 5% Dextrose, 0.9% Saline 2 mg/ml doxorubicin.HCl solutions were prepared in the following I=0.05 buffers: a) glycine.HCl pH 2.0, 2.5 and 3.0; b) formate pH 3.5; c) acetate pH 4.0, 5.0 and 5.5.

5.0 ml of each solution in glass vials were stored at 55° C. and analyzed at prefixed times (up to 120 hours) for doxorubicin.HCl assay and pH.

Tables 4, 5 and 6 give the doxorubicin.HCl residual concentration and percent stability at 55° C., at different pH's and times of storage for sterile water, 5% dextrose and 0.9% saline solutions, respectively.

The doxorubicin.HCl assays are the mean of three independent determinations performed by the USP HPLC method (USP XXI). At each pH value, the pseudo-first order rate constants ($K_{obs}$) for the degradation were calculated by linear regression analysis of the natural logarithm of the residual concentration of doxorubicin.HCl ($|Dx|_t$) versus time as depicted by the following equation:

$$\ln|Dx|_t = \ln|Dx| - K_{obs} \cdot t$$

J. Thuro Carstensen, Theory of Pharmaceutical Systems, Volume 1/General Principles, page 172, Academic Press, New York and London 1972

Kenneth A. Connors, Gordon L. Amidon, Lloyd Kennon, Chemical Stability of Pharmaceuticals, chapter 2, John Wiley and Sons, New York 1979

Arthur Osol, Remington's Pharmaceutical Sciences, 16th Edition, chapter 18, Mack Publishing Company, Easton, Pa. 1980

Valentino J. Stella, Chemical and Physical Bases Determining the Instability and Incompatibility of Formulated Injectable Drugs, Journal of Parenteral Sciences & Technology, July–August 1986, page 142.

Tables 7, 8 and 9 give the observed rate constants ($K_{obs}$) for the degradation kinetics of doxorubicin.HCl at 55° C. and at different pH's for sterile water, 5% dextrose and 0.9% saline solutions, respectively.

Figure 2:
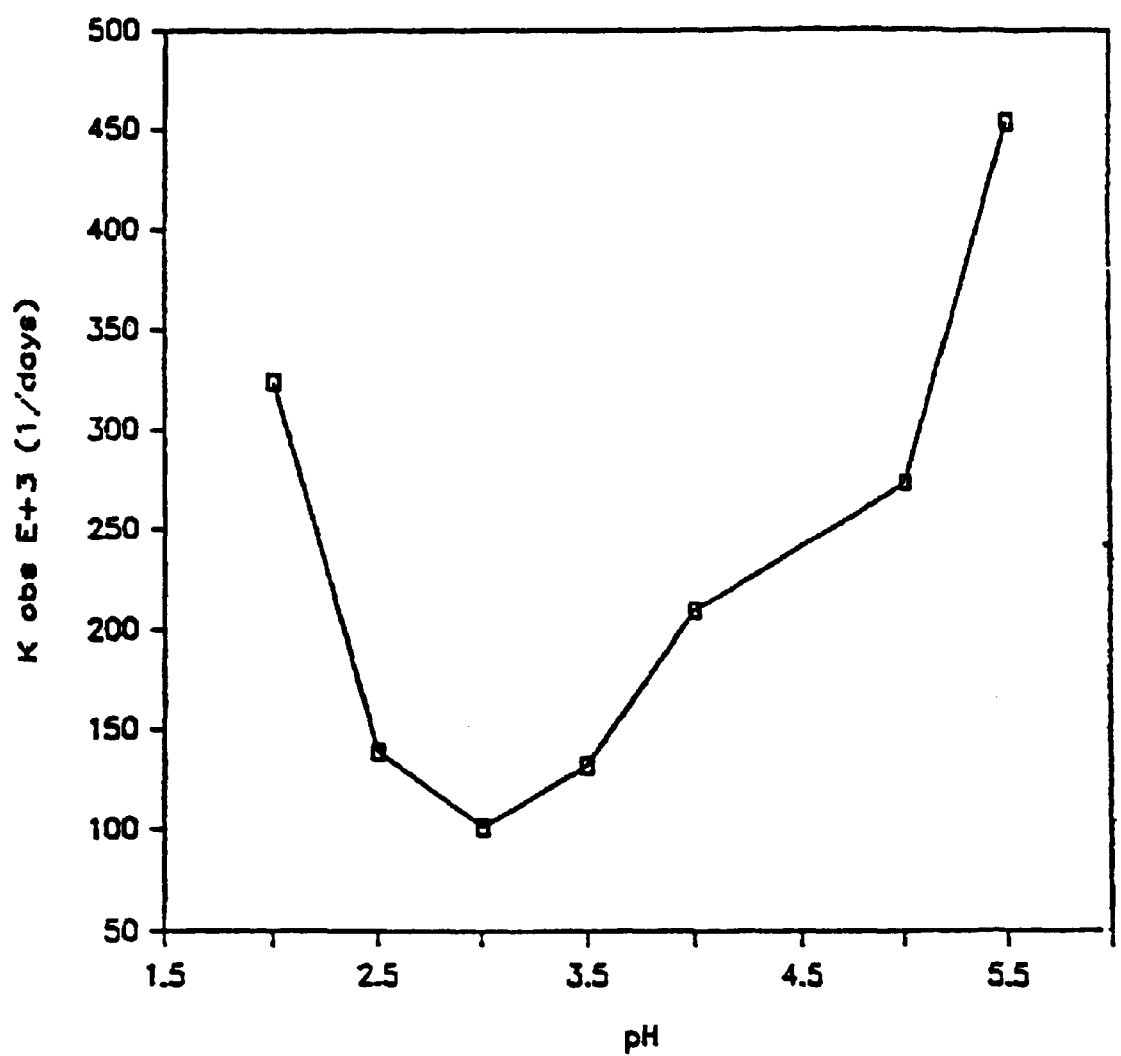
FIG. 2 is a $K_{obs}$ pH profile for doxorubicin.HCl degradation at 55° C. in 5% dextrose.
Figure 3:
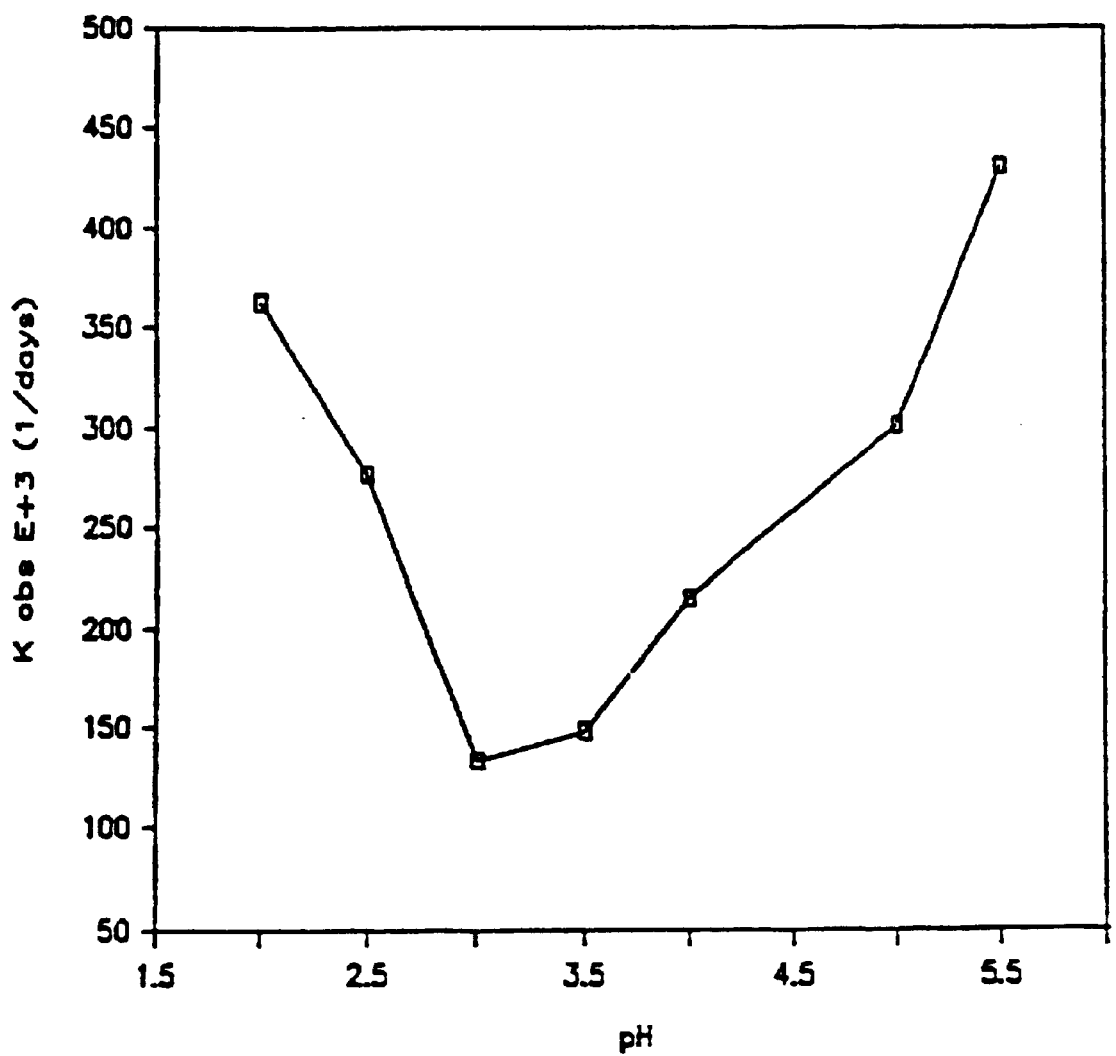
FIG. 3 is a $K_{obs}$ pH profile for doxorubicin.HCl degradation at 55° C. in 0.9% saline.

FIGS. 1, 2, and 3 show the $K_{obs}$–pH profile for the doxorubicin.HCl degradation at 55° C. in the above mentioned media. The data in Tables 4–9 and the FIGS. 1–3 evidence that the 2 mg/ml doxorubicin.HCl solutions show at 55° C. the maximum stability in the pH range about 3.0–3.5 (±0.2, e.g., 2.8, 3.2 and 3.3, 3.7) for all the three media tested. The range of from 2.5 to 3.0 is also a range of notable stability.

A common behavior as to stability is thus evidenced for aqueous solutions in general, since no practical differences in stability are observed when going from sterile water as such to sterile water containing a tonicity adjustment agent, either ionic, such as, e.g., sodium chloride, or non-ionic, such as, e.g., dextrose.

TABLE 4

Accelerated (55° C.) stability data of 2 mg/ml doxorubicin·HCl solutions in sterile water at various pHs

| Buffers | Tests | Time (hours) | | | | | | |
|---|---|---|---|---|---|---|---|---|
| | | 0 | 8 | 16 | 24 | 48 | 72 | 120 |
| pH 2.0 glycine-HCl | Doxorubicin·HCl assay ·mg/ml | 2.022 | 1.892 | 1.669 | 1.554 | 1.145 | 0.801 | |
| | ·% stability | 100.0 | 93.6 | 82.6 | 76.9 | 56.6 | 39.6 | |
| | pH | 2.00 | 2.01 | 2.02 | 2.01 | 2.01 | 2.02 | |
| pH 2.5 glycine-HCl | Doxorubicin·HCl assay mg/ml | 1.992 | 1.926 | 1.835 | 1.718 | 1.557 | 1.00 | |
| | % stability | 100.0 | 96.7 | 92.1 | 86.2 | 78.2 | 50.2 | |
| | pH | 2.51 | 2.50 | 2.50 | 2.52 | 2.51 | 2.52 | |
| pH 3.0 glycine-HCl | Doxorubicin·HCl assay mg/ml | 2.003 | 1.958 | 1.881 | 1.831 | 1.696 | 1.525 | 1.258 |
| | % stability | 100.0 | 97.8 | 93.9 | 91.4 | 84.7 | 76.1 | 62.8 |
| | pH | 3.00 | 3.03 | 3.02 | 3.02 | 3.01 | 3.02 | 3.00 |
| pH 3.5 formate | Doxorubicin·HCl assay mg/ml | 2.035 | 1.950 | 1.887 | 1.840 | 1.650 | 1.538 | 1.241 |
| | % stability | 100.0 | 95.8 | 92.7 | 90.4 | 81.1 | 75.6 | 61.0 |
| | pH | 3.51 | 3.51 | 3.51 | 3.51 | 3.52 | 3.52 | 3.51 |
| pH 4.0 acetate | Doxorubicin·HCl assay mg/ml | 2.032 | 1.788 | 1.681 | 1.561 | 1.167 | | |
| | % stability | 100.0 | 88.0 | 82.7 | 76.8 | 57.4 | | |
| | pH | 4.00 | 4.00 | 4.04 | 4.02 | 4.02 | | |
| pH 5.0 acetate | Doxorubicin·HCl assay mg/ml | 2.019 | 1.823 | 1.688 | 1.512 | 1.060 | | |
| | stability | 100.0 | 90.3 | 83.6 | 74.9 | 52.5 | | |
| | pH | 5.03 | 5.05 | 5.04 | 5.04 | 5.05 | | |
| pH 5.5 acetate | Doxorubicin·HCl assay mg/ml | 2.047 | 1.808 | 1.427 | 1.228 | 0.903 | | |
| | % stability | 100.0 | 88.3 | 69.7 | 60.0 | 44.1 | | |
| | pH | 5.50 | 5.53 | 5.53 | 5.54 | 5.56 | | |

TABLE 5

Accelerated (55° C.) stability data of 2 mg/ml doxorubicin·HCl solutions in 5% dextrose at various pHs

| Buffers | Tests | Time (hours) | | | | | | | | |
|---|---|---|---|---|---|---|---|---|---|---|
| | | 0 | 8 | 16 | 24 | 34 | 48 | 72 | 96 | 120 |
| pH 2.0 glycine-HCl | Doxorubicin·HCl assay mg/ml | 1.993 | 1.851 | 1.683 | 1.513 | 1.361 | 1.078 | 0.765 | | |
| | % stability | 100.0 | 92.8 | 84.4 | 75.9 | 68.3 | 54.1 | 38.4 | | |
| | pH | 2.14 | 2.13 | 2.14 | 2.15 | 2.18 | 2.21 | 2.16 | | |
| pH 2.5 glycine-HCl | Doxorubicin·HCl assay mg/ml | 1.967 | 1.897 | 1.822 | 1.760 | 1.682 | 1.499 | 1.305 | | |
| | % stability | 100.0 | 96.4 | 92.6 | 89.5 | 85.5 | 76.2 | 66.3 | | |
| | pH | 2.56 | 2.56 | 2.56 | 2.58 | 2.60 | 2.56 | 2.61 | | |
| pH 3.0 glycine-HCl | Doxorubicin·HCl assay mg/ml | 1.975 | | 1.908 | 1.832 | | 1.645 | 1.508 | 1.344 | 1.206 |
| | % stability | 100.0 | | 96.6 | 92.7 | | 83.3 | 76.4 | 68.0 | 61.1 |
| | pH | 3.04 | | 3.05 | 3.05 | | 3.06 | 3.00 | 3.13 | 3.10 |
| pH 3.5 formate | Doxorubicin·HCl assay mg/ml | 1.983 | | 1.897 | 1.858 | | 1.622 | 1.324 | 1.222 | |
| | % stability | 100.0 | | 95.7 | 93.7 | | 81.8 | 66.8 | 61.6 | |
| | pH | 3.58 | | 3.59 | 3.60 | | 3.63 | 3.60 | 3.63 | |
| pH 4.0 acetate | Doxorubicin·HCl assay mg/ml | 2.003 | 1.913 | 7.716 | 1.665 | 1.487 | 1.312 | 1.081 | | |
| | % stability | 100.0 | 95.5 | 85.6 | 83.1 | 74.2 | 65.5 | 53.9 | | |
| | pH | 4.10 | 4.10 | 4.11 | 4.11 | 4.16 | 4.15 | 4.12 | | |
| pH 5.0 acetate | Doxorubicin·HCl assay mg/ml | 2.012 | 1.906 | 1.673 | 1.608 | 1.416 | 1.163 | | | |
| | % stability | 100.0 | 94.7 | 83.2 | 79.9 | 70.4 | 57.8 | | | |
| | pH | 5.06 | 5.06 | 5.06 | 5.06 | 5.07 | 5.04 | | | |
| pH 5.5 acetate | Doxorubicin·HCl assay mg/ml | 1.991 | 1.841 | 1.470 | 1.246 | 1.091 | | | | |
| | % stability | 100.0 | 92.5 | 73.8 | 62.6 | 54.8 | | | | |
| | pH | 5.56 | 5.54 | 5.48 | 5.50 | 5.46 | | | | |

TABLE 6

Accelerated (55° C.) stability data of 2 mg/ml doxorubicin·HCl solutions in 0.9% saline at various pHs

| Buffers | Tests | Time (hours) | | | | | | | | | |
|---|---|---|---|---|---|---|---|---|---|---|---|
| | | 0 | 4 | 8 | 16 | 24 | 34 | 48 | 72 | 96 | 120 |
| pH 2.0 glycine-HCl | Doxorubicin·HCl assay mg/ml | 1.998 | | 1.857 | 1.580 | 1.397 | 1.231 | 0.931 | 0.701 | | |
| | % stability | 100.0 | | 92.9 | 79.1 | 69.9 | 61.6 | 46.6 | 35.1 | | |
| | pH | 2.16 | | 2.16 | 2.18 | 2.16 | 2.22 | 2.20 | 2.19 | | |
| pH 2.5 glycine-HCl | Doxorubicin·HCl assay mg/ml | 1.946 | | 1.875 | 1.670 | 1.602 | 1.368 | 1.132 | | | |
| | % stability | 100.0 | | 96.3 | 85.8 | 82.3 | 70.3 | 58.1 | | | |
| | pH | 2.59 | | 2.59 | 2.59 | 2.58 | 2.62 | 2.62 | | | |
| pH 3.0 glycine-HCl | Doxorubicin·HCl assay mg/ml | 1.994 | | | 1.818 | 1.771 | | 1.571 | 1.375 | 1.205 | 1.003 |
| | % stability | 100.0 | | | 91.2 | 88.8 | | 78.8 | 69.0 | 60.4 | 50.3 |
| | pH | 3.06 | | | 3.07 | 3.07 | | 3.08 | 3.13 | 3.14 | 3.12 |
| pH 3.5 formate | Doxorubicin·HCl assay mg/ml | 1.997 | | | 1.824 | 1.742 | | 1.543 | 1.323 | 1.176 | 0.919 |
| | % stability | 100.0 | | | 91.4 | 87.2 | | 77.3 | 66.2 | 58.9 | 46.0 |
| | pH | 3.58 | | | 3.56 | 3.56 | | 3.66 | 3.61 | 3.64 | 3.63 |
| pH 4.0 acetate | Doxorubicin·HCl assay mg/ml | 1.972 | 1.885 | 1.828 | 1.653 | 1.594 | | | | | |
| | % stability | 100.0 | 95.6 | 92.7 | 83.8 | 80.8 | | | | | |
| | pH | 4.10 | 4.10 | 4.10 | 4.10 | 4.11 | | | | | |
| pH 5.0 acetate | Doxorubicin·HCl assay mg/ml | 1.979 | | 1.732 | 1.469 | 1.442 | 1.278 | | | | |
| | % stability | 100.0 | | 87.5 | 74.2 | 72.8 | 64.6 | | | | |
| | pH | 5.04 | | 5.06 | 5.04 | 5.05 | 5.05 | | | | |
| pH 5.5 acetate | Doxorubicin·HCl assay mg/ml | 2.023 | | 1.847 | 1.548 | 1.330 | | | | | |
| | % stability | 100.0 | | 91.3 | 76.5 | 65.7 | | | | | |
| | pH | 5.58 | | 5.56 | 5.55 | 5.53 | | | | | |

TABLE 7

$K_{obs}$ values (1/days) for the degradation of doxorubicin·HCl 2 mg/ml solutions in sterile water at various pHs at 55° C.

| Buffer | pH | $K_{obs} \times 10^3$ | 95% confidence limits |
|---|---|---|---|
| Glycine-HCl (I = 0.05) | 2.0 | 309.5 | ±12.6 |
| Glycine-HCl (I = 0.05) | 2.5 | 138.3 | ±0.6 |
| Glycine-HCl (I = 0.05) | 3.0 | 93.1 | ±4.6 |
| Formate (I = 0.05) | 3.5 | 96.7 | ±4.4 |
| Acetate (I = 0.05) | 4.0 | 269.8 | ±18.7 |
| Acetate (I = 0.05) | 5.0 | 322.6 | ±19.2 |
| Acetate (I = 0.05) | 5.5 | 415.4 | ±45.7 |

TABLE 8

$K_{obs}$ values (1/days) for the degradation of doxorubicin·HCl 2 mg/ml solutions in 5% dextrose at various pHs at 55° C.

| Buffer | pH | $K_{obs} \times 10^3$ | 95% confidence limits |
|---|---|---|---|
| Glycine-HCl (I = 0.05) | 2.0 | 323.8 | ±17.2 |
| Glycine-HCl (I = 0.05) | 2.5 | 138.7 | ±9.9 |
| Glycine-HCl (I = 0.05) | 3.0 | 100.5 | ±5.9 |
| Formate (I = 0.05) | 3.5 | 132.0 | ±20.7 |
| Acetate (I = 0.05) | 4.0 | 209.7 | ±12.7 |
| Acetate (I = 0.05) | 5.0 | 273.1 | ±27.7 |
| Acetate (I = 0.05) | 5.5 | 453.7 | ±59.2 |

TABLE 9

$K_{obs}$ values (1/days) for the degradation of doxorubicin·HCl 2 mg/ml solutions in 0.9% saline at various pHs at 55° C.

| Buffer | pH | $K_{obs} \times 10^3$ | 95% confidence limits |
|---|---|---|---|
| Glycine-HCl (I = 0.05) | 2.0 | 362.4 | ±19.4 |
| Glycine-HCl (I = 0.05) | 2.5 | 276.5 | ±30.2 |
| Glycine-HCl (I = 0.05) | 3.0 | 133.2 | ±8.0 |
| Formate (I = 0.05) | 3.5 | 148.1 | ±11.1 |
| Acetate (I = 0.05) | 4.0 | 215.7 | ±35.4 |
| Acetate (I = 0.05) | 5.0 | 301.2 | ±60.1 |
| Acetate (I = 0.05) | 5.5 | 430.3 | ±69.9 |

Shelf-Life (t 90%) Forecast of Doxorubicin.HCl 2 mg/ml Sterile Water Solution Adjusted to pH 3.0

5.0 ml of doxorubicin.HCl 2 mg/ml aqueous solution adjusted to pH 3.0 with 0.5 N HCl were stored, in glass vials, at:

a) 55° C. for 21 days, b) 45° C. and 35° C. for 28 days, c) 27° C. for 90 days.

b) At prefixed times the vials were analyzed for doxorubicin.HCl assay and pH.

The logarithmic plots of the residual concentration versus time were linear and indicated the degradation of the drug to follow pseudo-first order kinetics at constant pH and temperature.

The observed rate constants ($K_{obs}$) for the degradation were calculated again by linear regression analysis of a plot of the natural logarithm of the residual concentration of doxorubicin.HCl ($|Dx|_t$) versus time as depicted by the equation previously reported:

$$\ln|Dx|_t = \ln|Dx|_o - K_{obs} \cdot t$$

The Arrhenius equation for the degradation process was calculated from the $K_{obs}$ obtained from the different temperatures taken in account for the testing (table 11).

Applying the equation, the rate constants for the pseudo-first order reactions at 4° C., 8° C., 15° C. and 27° C. were calculated, together with the expected $t_{90\%}$ at these temperatures.

Table 10 gives the doxorubicin.HCl residual concentration and percent stability at pH 3.0, at different temperatures and times of storage.

Figure 4:
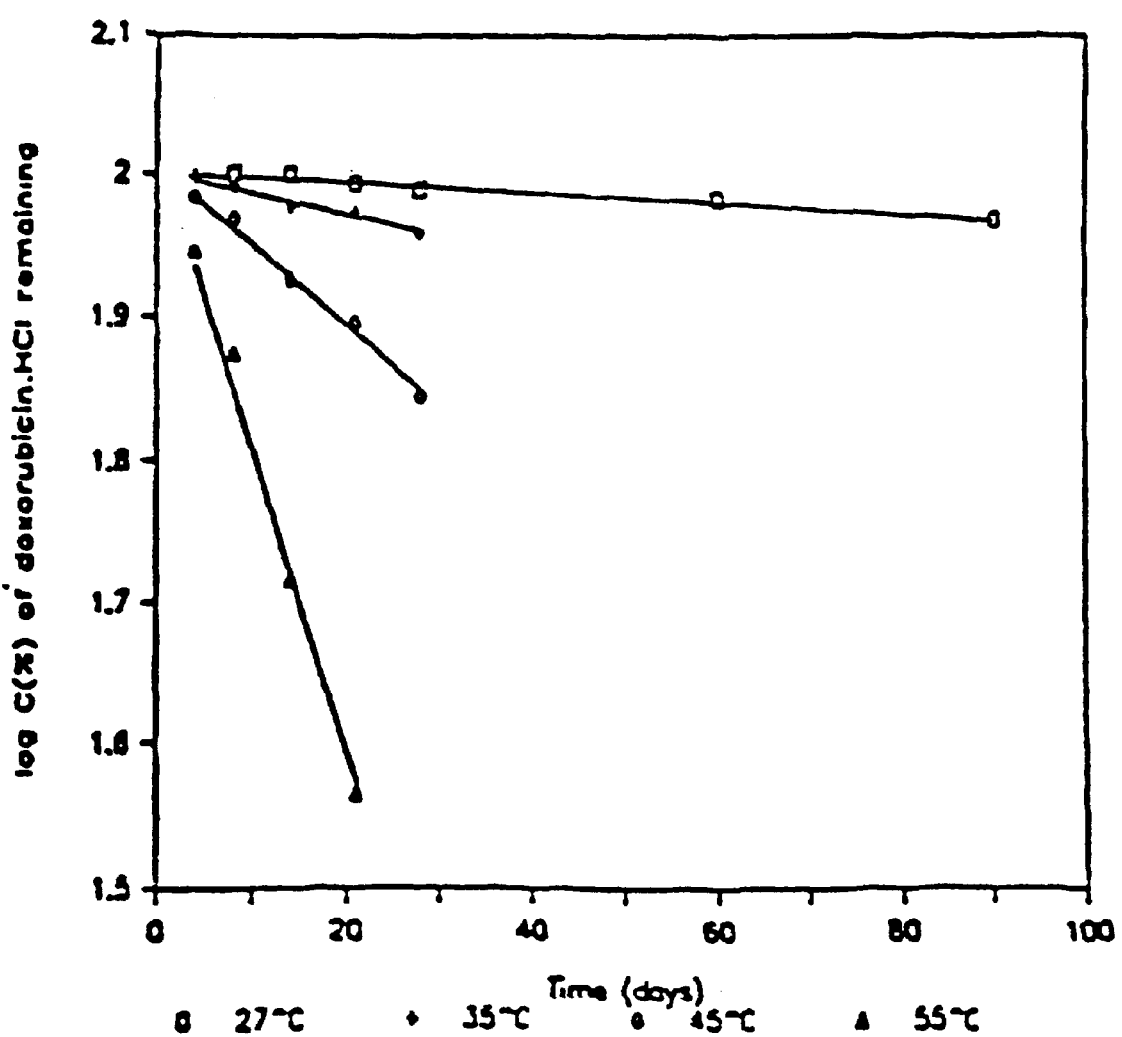
FIG. 4 is a logarithmic plot of residual doxorubicin.HCl concentration versus time.

FIG. 4 gives the logarithm of the remaining doxorubicin.HCl concentration versus time at different temperatures.

The $t_{90\%}$ forecasts (table 11) show that a commercially meaningful shelf-life can be attributed to doxorubicin.HCl 2 mg/ml pH 3.0 aqueous solution only if the product is stored in a refrigerator (between 2° C. and 8° C.).

TABLE 10

Accelerated stability data of doxorubicin·HCl 2 mg/ml pH 3.0 solutions in sterile water at different times and temperatures

| Storage Temperature | Tests | Time (days) | | | | | | | |
|---|---|---|---|---|---|---|---|---|---|
| | | 0 | 4 | 8 | 14 | 32 | 28 | 60 | 90 |
| 27° C. | Doxorubicin·HCl assay mg/ml | 1.992 | | 1.993 | 1.988 | 1.962 | 1.941 | 1.908 | 1.850 |
| | % stability | 100.0 | | 100.1 | 99.8 | 98.5 | 97.4 | 95.8 | 92.9 |
| | pH | 3.00 | | 2.95 | 2.94 | 2.95 | 2.94 | 2.96 | 2.93 |
| | Doxorubicin·HCl assay | | | | | | | | |

TABLE 10-continued

Accelerated stability data of doxorubicin·HCl 2 mg/ml pH 3.0 solutions in sterile water at different times and temperatures

| Storage Temperature | Tests | Time (days) | | | | | | | |
|---|---|---|---|---|---|---|---|---|---|
| | | 0 | 4 | 8 | 14 | 32 | 28 | 60 | 90 |
| 35° C. | mg/ml | 1.992 | 1.985 | 1.952 | 1.889 | 1.876 | 1.808 | | |
| | % stability | 100.0 | 99.6 | 98.0 | 94.8 | 94.2 | 90.8 | | |
| | pH | 3.00 | 2.96 | 2.98 | 2.93 | 2.92 | 2.92 | | |
| | Doxorubicin·HCl assay | | | | | | | | |
| 45° C. | mg/ml | 1.992 | 1.919 | 1.851 | 1.677 | 1.565 | 1.393 | | |
| | % stability | 100.0 | 96.3 | 92.9 | 84.2 | 78.6 | 69.9 | | |
| | pH | 3.00 | 2.97 | 2.95 | 2.85 | 2.92 | 2.90 | | |
| | Doxorubicin·HCl assay | | | | | | | | |
| 55° C. | mg/ml | 1.992 | 1.760 | 1.493 | 1.036 | 0.730 | | | |
| | % stability | 100.0 | 88.4 | 74.9 | 52.0 | 36.6 | | | |
| | pH | 3.00 | 2.94 | 2.90 | 2.80 | 2.82 | | | |

TABLE 11

Arrhenius approach. Pseudo-first order rate constants, Arrhenius equation, calculated $t_{90\%}$ PSEUDO-FIRST ORDER RATE CONSTANTS, OBSERVED VALUES ($K_{obs}$)

| Temperature | $K_{obs} \times 10^3$ (1/days) | Correlation Coefficient |
|---|---|---|
| 27° C. | 0.850 | 0.986 |
| 35° C. | 3.506 | 0.983 |
| 45° C. | 12.790 | 0.995 |
| 55° C. | 49.340 | 0.995 |

ARRHENIUS EQUATION FROM 27° C., 35° C., 45° C., AND 55° C. RATE CONSTANTS
ln $K_{obs}$ = −14083/T + 39.95
correlation coefficient = 0.9988
PSEUDO-FIRST ORDER RATE CONSTANTS, CALCULATED VALUES (K)

| Temperature | $K \times 10^3$ (1/days) | $t_{90\%}$ (days) | 95% confidence limits |
|---|---|---|---|
| 4° C. | 0.019 | 5,652 | 3,079–10,380 |
| 8° C. | 0.038 | 2,745 | 1,603–4,697 |
| 15° C. | 0.130 | 810 | 532–1,238 |
| 27° C. | 0.918 | 115 | 89–147 |

Shelf-Life (t 90%) Forecast of Doxorubicin.HCl 2 mg/ml 0.9% Sodium Chloride Solution Adjusted to pH 3.0

5.0 ml of doxorubicin.HCl 2 mg/ml solution in 0.9% sodium chloride adjusted to pH 3.0 with 0.5 N HCl were stored, in glass vials, at: a) 60° C. for 4 days, b) 55° C. for 14 days, c) 45° C. for 21 days, d) 35° C. for 28 days.

At prefixed times the vials were analyzed for doxorubicin.HCl assay and pH.

The logarithmic plots of the residual concentration versus time were linear and indicated the degradation of the drug to follow pseudo-first order kinetics at constant pH and temperature.

The observed rate constants ($K_{obs}$) for the degradation were calculated again by linear regression analysis of a plot of the natural logarithm of the residual concentration of doxorubicin.HCl ($|Dx|_t$) versus time as depicted by the equation previously reported:

$$\ln|Dx|_t = \ln|Dx|_o - K_{obs} \cdot t$$

The Arrhenius equation for the degradation process was calculated from the $K_{obs}$ obtained from the different temperatures taken in account for the testing (table 13).

Applying the equation, the rate constants for the pseudo-first order reactions at 4° C., 8° C., 15° C. and 27° C. were calculated, together with the expected $t_{90\%}$ at these temperatures.

Table 12 gives the doxorubicin.HCl residual concentration and percent stability at pH 3.0, at different temperatures and times of storage.

Figure 5:
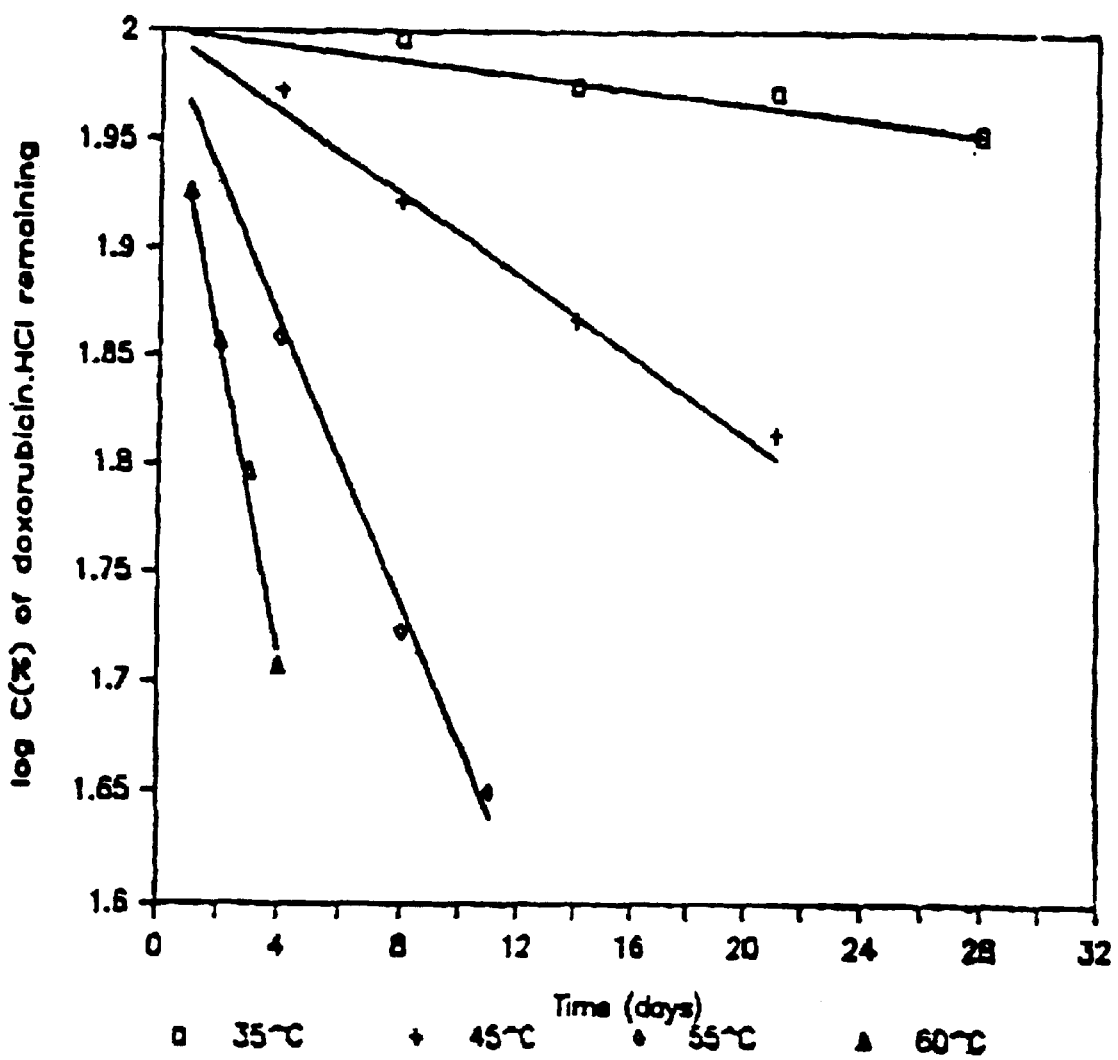
FIG. 5 is a logarithmic plot of residual doxorubicin.HCl concentration in 0.9% NaCl.

FIG. 5 gives the logarithm of the remaining doxorubicin-.HCl concentration versus time at different temperatures.

TABLE 12

Accelerated stability data of doxorubicin·HCl 2 mg/ml in 0.9% sodium chloride at different times and temperatures

| Storage Conditions | Tests | Time (days) | | | | | | | | | |
|---|---|---|---|---|---|---|---|---|---|---|---|
| | | 0 | 1 | 2 | 3 | 4 | 8 | 11 | 14 | 21 | 28 |
| 35° C. | Doxorubicin·HCl assay | | | | | | | | | | |
| | mg/ml | 2.061 | | | | | 2.045 | | 1.946 | 1.932 | 1.852 |
| | % stability | 100.0 | | | | | 99.2 | | 94.4 | 93.7 | 89.9 |
| | pH | 3.05 | | | | | 2.98 | | 2.92 | 2.92 | 2.98 |
| 45° C. | Doxorubicin·HCl assay | | | | | | | | | | |
| | mg/ml | 2.061 | | | | 1.996 | 1.724 | | 1.517 | 1.344 | |
| | % stability | 100.0 | | | | 96.5 | 83.6 | | 73.6 | 65.2 | |
| | pH | 3.05 | | | | 2.98 | 2.97 | | 2.98 | 2.93 | |
| 55° C. | Doxorubicin·HCl assay | | | | | | | | | | |
| | mg/ml | 2.061 | | | | 1.450 | 1.066 | 0.900 | | | |
| | % stability | 100.0 | | | | 70.4 | 51.7 | 43.7 | | | |

TABLE 12-continued

Accelerated stability data of doxorubicin·HCl 2 mg/ml in 0.9% sodium chloride at different times and temperatures

| Storage Conditions | Tests | Time (days) | | | | | | | | |
|---|---|---|---|---|---|---|---|---|---|---|
| | | 0 | 1 | 2 | 3 | 4 | 8 | 11 | 14 | 21 | 28 |
| | pH | 3.05 | | | | 2.90 | 2.97 | 2.95 | | | |
| | Doxorubicin·HCl assay | | | | | | | | | | |
| 60° C. | mg/ml | 2.061 | 1.742 | 1.481 | 1.290 | 1.050 | | | | | |
| | % stability | 100.0 | 84.5 | 71.9 | 62.6 | 50.9 | | | | | |
| | pH | 3.05 | 2.97 | 2.96 | 2.98 | 2.96 | | | | | |

The $t_{90\%}$ forecasts (table 13) show that a commercially meaningful shelf-life can be attributed to doxorubicin.HCl 2 mg/ml pH 3.0 solution in 0.9% sodium chloride only if the product is stored in a refrigerator (between 2° C. and 8° C.).

TABLE 13

Doxorubicin·HCl 2 mg/ml pH 3.0 solution in 0.9% NaCl
Arrhenius approach. Pseudo-first order rate constants,
Arrhenius equation, calculated $t_{90\%}$ PSEUDO-FIRST ORDER RATE CONSTANTS, OBSERVED VALUES ($K_{obs}$)

| Temperature | $K_{obs} \times 10^3$ (1/days) | Correlation Coefficient |
|---|---|---|
| 35° C. | 3.89 | 0.965 |
| 45° C. | 21.61 | 0.987 |
| 55° C. | 75.90 | 0.996 |
| 60° C. | 164.90 | 0.998 |

ARRHENIUS EQUATION FROM 35° C., 45° C., 55° C. AND 60° C. RATE CONSTANTS
ln $K_{obs}$ = −15100/T + 43.53
correlation coefficient = 0.9986

PSEUDO-FIRST ORDER RATE CONSTANTS, CALCULATED VALUES (K)

| Temperature | $K \times 10^3$ (1/days) | $t_{90\%}$ (days) | 95% confidence limits |
|---|---|---|---|
| 4° C. | 0.017 | 6,166 | 1,670–22,756 |
| 8° C. | 0.037 | 2,838 | 861–9,351 |
| 15° C. | 0.137 | 768 | 281–2,105 |
| 27° C. | 1.112 | 94 | 45–197 |

Shelf-Life (t 90%) Forecast of Doxorubicin.HCl 2 mg/ml Solution in 5% Dextrose Adjusted to pH 3.0

5.0 ml of doxorubicin.HCl 2 mg/ml solution in 5% dextrose adjusted to pH 3.0 with 0.5 N HCl were stored, in glass vials, at: a) 60° C. for 8 days, b) 55° C. for 17 days, c) 45° C. and 35° C. for 28 days.

At prefixed times the vials were analyzed for doxorubicin.HCl assay and pH.

The logarithmic plots of the residual concentration versus time were linear and indicated the degradation of the drug to follow pseudo-first order kinetics at constant pH and temperature. The observed rate constants ($K_{obs}$) for the degradation was calculated again by linear regression analysis of a plot of the natural logarithm of the residual concentration of doxorubicin.HCl ($|Dx|_t$) versus time as depicted by the equation previously reported:

$$\ln|Dx|_t = \ln|Dx|_o - K_{obs} \cdot t$$

The Arrhenius equation for the degradation process was calculated from the $K_{obs}$ obtained from the different temperatures taken in account for the testing (table 15).

Applying the equation, the rate constants for the pseudo-first order reactions at 4° C., 8° C., and 15° C. and 27° C. were calculated, together with the expected $t_{90\%}$ at these temperatures.

Table 14 gives the doxorubicin.HCl residual concentration and percent stability at pH 3.0, at different temperatures and times of storage.

Figure 6:
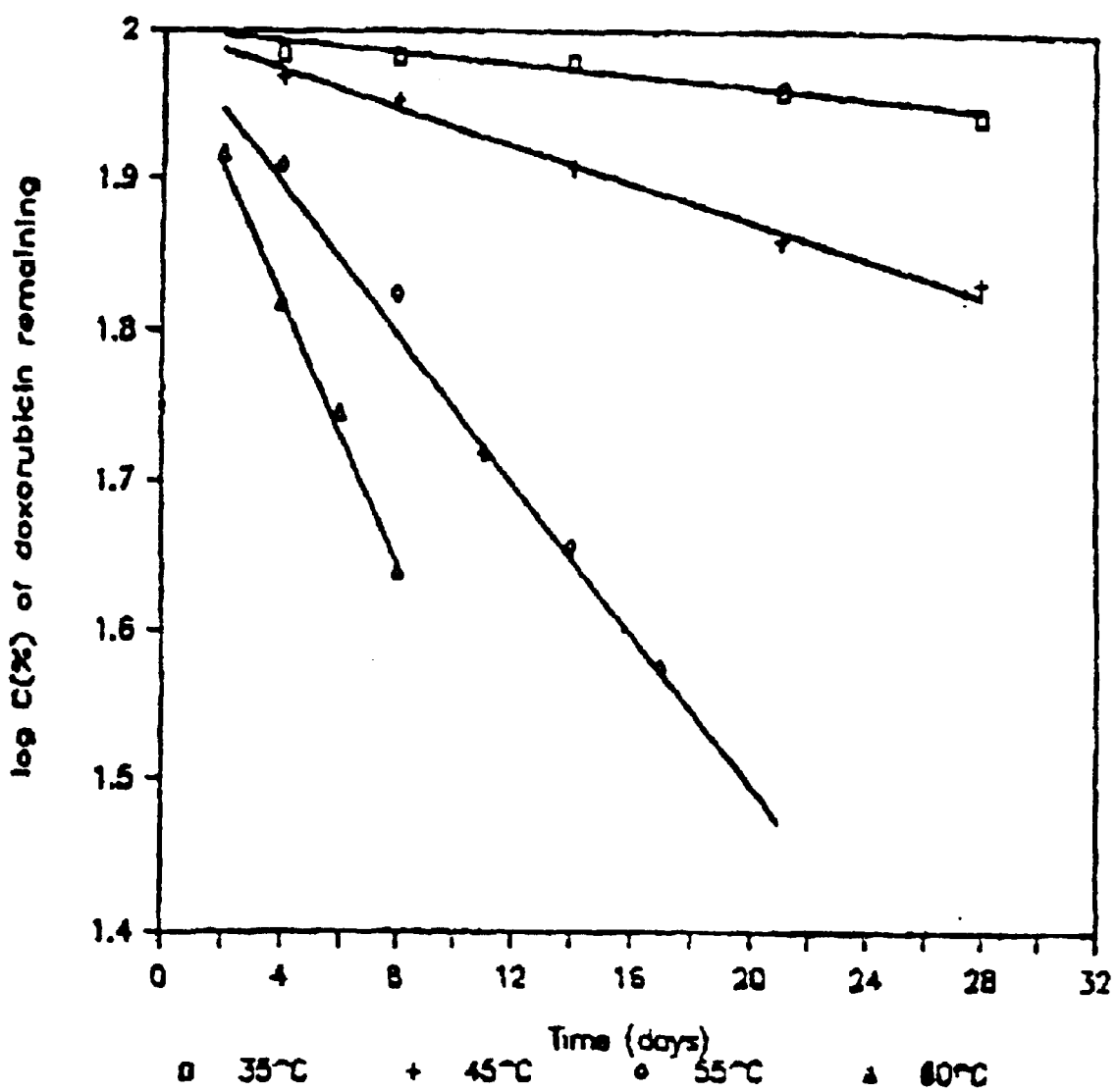
FIG. 6 is a logarithmic plot of residual doxorubicin.HCl concentration in 5% dextrose.

FIG. 6 gives the logarithm of the remaining doxorubicin-.HCl concentration versus time at different temperatures.

The $t_{90\%}$ forecasts (table 15) show that a commercially meaningful shelf-life can be attributed to doxorubicin.HCl 2 mg/ml pH 3.0 5% dextrose solution only if the product is stored in a refrigerator (between 2° C. and 8° C.).

TABLE 14

Accelerated stability data of doxorubicin·HCl 2 mg/ml pH 3.0 solution in 5% dextrose at different times and temperatures

| Storage Conditions | Tests | Time (days) | | | | | | | | |
|---|---|---|---|---|---|---|---|---|---|---|
| 28 | | 0 | 2 | 4 | 6 | 8 | 11 | 14 | 17 | 21 |
| | Doxorubicin·HCl assay | | | | | | | | | |
| 35° C. | mg/ml | 2.114 | | 2.044 | | 2.034 | | 2.015 | 1.934 | 1.859 |
| | % stability | 100.0 | | 96.7 | | 96.2 | | 53.3 | 91.5 | 87.9 |
| | pH | 3.02 | | 2.98 | | 2.94 | | 2.95 | 2.90 | 2.94 |
| | Doxorubicin·HCl assay | | | | | | | | | |
| 45° C. | mg/ml | 2.114 | | 1.940 | | 1.870 | | 1.684 | 1.510 | 1.410 |
| | % stability | 100.0 | | 91.8 | | 88.5 | | 79.7 | 71.5 | 66.7 |
| | pH | 3.02 | | 2.97 | | 2.98 | | 2.95 | 2.96 | 2.96 |
| | Doxorubicin·HCl assay | | | | | | | | | |
| 55° C. | mg/ml | 2.114 | | 1.718 | | 1.415 | | 1.112 | 0.957 | 0.796 |
| | % stability | 100.0 | | 81.3 | | 66.9 | | 52.6 | 45.3 | 37.7 |
| | pH | 3.02 | | 2.95 | | 2.92 | | 2.99 | 2.91 | 2.95 |
| | Doxorubicin·HCl assay | | | | | | | | | |

TABLE 14-continued

Accelerated stability data of doxorubicin·HCl 2 mg/ml pH 3.0 solution in 5% dextrose at different times and temperatures

| Storage Conditions | | Time (days) | | | | | | | | |
|---|---|---|---|---|---|---|---|---|---|---|
| 28 | Tests | 0 | 2 | 4 | 6 | 8 | 11 | 14 | 17 | 21 |
| 60° C. | mg/ml | 2.114 | 1.752 | 1.393 | 1.176 | 0.925 | | | | |
| | % stability | 100.0 | 82.9 | 65.9 | 55.7 | 43.8 | | | | |
| | pH | 3.02 | 2.96 | 2.98 | 2.96 | 2.97 | | | | |

TABLE 15

Doxorubicin·HCl 2 mg/ml pH 3.0 solution in 5% dextrose. Arrhenius approach. Pseudo-first order rate constants, Arrhenius equation, calculated $t_{90\%}$

| PSEUDO-FIRST ORDER RATE CONSTANTS, OBSERVED VALUES ($K_{obs}$) | | |
|---|---|---|
| Temperature | $K_{obs} \times 10^3$ (1/days) | Correlation Coefficient |
| 35° C. | 4.190 | 0.990 |
| 45° C. | 14.55 | 0.995 |
| 55° C. | 58.11 | 0.998 |
| 60° C. | 102.6 | 0.999 |

ARRHENIUS EQUATION FROM 35° C., 45° C., 55° C. AND 60° C. RATE CONSTANTS
ln $K_{obs}$ = −13266/T + 37.56
correlation coefficient = 0.9993
PSEUDO-FIRST ORDER RATE CONSTANTS, CALCULATED VALUES (K)

| Temperature | $K \times 10^3$ (1/days) | $t_{90\%}$ (days) | 95% confidence limits |
|---|---|---|---|
| 4° C. | 0.0326 | 3,218 | 1,463–7,082 |
| 8° C. | 0.0645 | 1,628 | 792–3,344 |
| 15° C. | 0.203 | 516 | 281–949 |
| 27° C. | 1.283 | 82 | 53–128 |

Long Term Stability of Doxorubicin Formulations Having a pH Falling Within the Range From 2.5 to 3.5.

Batches tested, formulations tested and packaging used are reported on, respectively, tables 16, 17 and 18, as well as on, respectively, tables 25, 26 and 27.

Test and Methods

The formulations were tested as regards appearance, clarity of solution, pH, sterility (8° C., yearly), doxorubicin-.HCl assay.

Test Methods

For appearance and clarity; visual inspection

For pH: USP XXI

For sterility; USP XXI (membrane filtration)

For doxorubicin.HCl assay: HPLC ion-pair method and USP HPLC method (USP XXI)

Brief description of the HPLC ion-pair method for doxorubicin.

HCl assay:

Column filling: reverse phase, Zortax TMS

Mobile phase: water, acetonitrile, methanol (54:29:17 v/v/v) containing 2 ml/l 85% phosphoric acid and 1 mg/ml sodium laurylsulfate (pairing agent) adjusted to pH 3.5 with 2N NaOH Mobile phase flow rate: 1.5 ml/min Column temperature: ambient (22° C.±2° C.)

Analytical wavelength: 254 nm

System suitability parameters: Symmetry factor between 0.7 and 1.2; number of theoretical plates ≧2500; measurement reproducibility: variation coefficient <1, n=6; resolution factor ≧12

The HPLC ion-pair method for doxorubicin.HCl assay is validated for accuracy, precision, linearity, sensitivity, specificity and stability-indicating nature.

The results obtained for:

percent doxorubicin.HCl stability (ion-pair method) and pH referred to the vials stored in upright position are given in:

Table 19 storage at −20° C.

Tables 20 and 28 storage at +4° C.

Tables 21 and 29 storage at +8° C.

Tables 22 and 30 storage at +15° C.

Tables 23 and 31 storage at +27° C.

Table 24 storage at 100 and 250 foot candles

Table 32 storage at 250 foot candles.

The doxorubicin.HCl assays given in these tables are the mean of three independent determinations.

As far as the other parameters checked during stability:

the clarity of the solution was unchanged at all the checks carried out at all the storage conditions applied;

the appearance of the solutions was: a) unchanged at all the checks carried out on samples stored at 4° C. and 8° C., b) slightly darkened after: 9 months at 15° C., 3 months at 27° C., 3 months at 100 and 250 foot candles light;

the closure system was unchanged at all the checks carried out at all the storage conditions;

the sterility was maintained after 18 months at 8° C.

The results of the controls carried out on the vials stored in inverted position do not differ significantly from those on the vials in upright position.

The percent doxorubicin.HCl stability values obtained by the USP HPLC method do not differ significantly from those obtained by the HPLC ion-pair method given in Tables 19–24.

The obtained stability data indicate that the tested doxorubicin.HCl solutions having different pH values within the range from 2.5 to 3.5 reach the lower limit of acceptance (90% of nominal concentration) in about 9 and 2–3 months at 15° C. and, respectively 27° C., but prove stable up to 18 months at 4° C. and 8° C., i.e. at temperature usually adopted for the storage of the products under refrigeration.

In distinct contrast, the doxorubicin.HCl solution obtained upon reconstitution of the commercial freeze-dried preparate, whose pH varies between 4.5 and 6, shows a much lower degree of stability as shown by the fact that it is recommended to discard reconstituted solutions after only 48 hours storage in refrigerator according to the leaflet accompanying packages of Adriamycin (i.e. doxorubicin.HCl) in the United States.

TABLE 16

Stability studies. Batches tested.

| Batch Characteristics | Batch No | | | | | | | |
|---|---|---|---|---|---|---|---|---|
| | TF/23049 | TF/23077 | TF/23078 | TF/23117 | TF/23119 | H0001 | L0O1 | M0001 |
| Doxorubicin·HCl per vial (mg) | 10 | 10 | 10 | 20 | 50 | 10 | 20 | 50 |
| pH | 3.06 | 2.81 | 3.50 | 2.97 | 3.08 | 3.15 | 3.05 | 3.20 |
| Formulation No. | F16804/IL1 | F16804/IL1 | F16804/IL1 | F16804/IL2 | F16804/IL3 | F16804/IL4 | F16804/IL5 | F16804/IL6 |
| Batch size No. of vials | 700 | 400 | 400 | 500 | 500 | 2,400 | 2,300 | 2,400 |

TABLE 17

Stability studies. Formulations tested.

| Composition per vial | Formulation number | | | | | |
|---|---|---|---|---|---|---|
| | F16804/IL | F16804/IL2 | F16804/IL3 | F16804/IL4 | F16804/IL5 | F16804/IL6 |
| Doxorubicin·HCl mg | 10 | 20 | 50 | 10 | 20 | 50 |
| Hydrochloric acid q.s. to pH | 2.8–3.5 | 2.8–3.5 | 2.8–3.5 | 2.8–3.5 | 2.8–3.5 | 2.8–3.5 |
| Water q.s. to ml | 5.0 | 10.0 | 25.0 | 5.0 | 10.0 | 25.0 |

TABLE 18

Stability studies. Packaging used.

| Packaging | Batch No. | | | | | | | |
|---|---|---|---|---|---|---|---|---|
| | TF/23049 | TF/23077 | TF/23078 | TF/231117 | TF/23119 | H0001 | L0001 | M0001 |
| vial glass type | I | I | I | I | I | I | I | I |
| vial top capacity | 8 ml | 8 ml | 8 ml | 14 ml | 39 ml | 10 ml | 14 ml | 39 ml |
| stopper | chlorobutyl rubber, teflon-faced | chlorobutyl rubber, teflon-faced | chlorobutyl rubber, teflon-faced | chlorobutyl rubber, teflon-faced | chlorobutyl rubber, teflon-faced | chlorobutyl rubber, teflon-faced | chlorobutyl rubber, teflon-faced | chlorobutyl rubber, teflon-faced |
| seal | aluminum | aluminum | aluminum | aluminum | aluminum | aluminum | aluminum | aluminum |

TABLE 19

Doxorubicin·HCl 2 mg/ml solution. Stability data at −20° C. (vials stored upright) acquired up to 3 months

| Batch Dosage | | Time-Months | | |
|---|---|---|---|---|
| | | 0 | 1 | 3 |
| H0001 10 mg | doxorubicin·HCl % stability | 100 | 99.9 | 99.6 |
| | pH | 3.15 | 3.12 | 2.98 |
| L0001 20 mg | doxorubicin·HCl % stability | 100 | 100.8 | 99.8 |
| | pH | 3.05 | 2.84 | 2.97 |
| M0001 50 mg | doxorubicin·HCl % stability | 100 | 100.7 | 101.0 |
| | pH | 3.20 | 2.96 | 2.99 |

TABLE 20

Doxorubicin·HCl 2 mg/ml solution. Stability data at 4° C. (vials stored upright) acquired up to 18 months

| Batch Dosage | Months | 0 | 1 | 3 | 6 | 9 | 12 | 18 |
|---|---|---|---|---|---|---|---|---|
| TF/23049 | * | 100 | 99.9 | 100.6 | 98.3 | 98.2 | 97.7 | 96.9 |
| 10 mg | ** | 3.06 | 3.10 | 3.09 | 3.10 | 3.05 | 2.97 | 3.07 |
| TF/23077 | * | 100 | 101.7 | 99.3 | 97.9 | 98.0 | 99.8 | |
| 10 mg | ** | 2.81 | 2.86 | 2.75 | 2.65 | 2.67 | 2.76 | |
| TF/23078 | * | 100 | 101.2 | 98.8 | 97.8 | 98.8 | 96.8 | |
| 10 mg | ** | 3.50 | 3.54 | 3.49 | 3.44 | 3.43 | 3.54 | |
| TF/23117 | * | 100 | 96.8 | 96.6 | 98.1 | 98.8 | 97.5 | |
| 20 mg | ** | 2.97 | 2.98 | 2.92 | 2.86 | 2.95 | 2.98 | |
| TF/23119 | * | 100 | 98.6 | 99.1 | 98.9 | 98.4 | 97.5 | |
| 50 mg | ** | 3.08 | 2.98 | 2.98 | 2.89 | 2.99 | 3.00 | |
| H0001 | * | 100 | | | 97.6 | 99.2 | | |
| 10 mg | ** | 3.15 | n.d. | | 3.06 | 3.22 | | |
| L000 | * | 100 | | | 98.8 | 98.4 | | |
| 20 mg | ** | 3.05 | n.d. | | 2.99 | 2.94 | | |
| M0001 | * | 100 | | | 99.7 | 99.7 | | |
| 50 mg | ** | 3.20 | n.d. | | 3.00 | 3.04 | | |

* doxorubicin·HCl % stability
** pH
n.d. = not determined

TABLE 21

Doxorubicin·HCl 2 mg/ml solution. Stability data at 8° C. (vials stored upright) acquired up to 18 months

| Batch Dosage | | 0 | 1 | 2 | 3 | 6 | 9 | 12 | 18 |
|---|---|---|---|---|---|---|---|---|---|
| TF/23049 | * | 100 | 99.7 | | | 100.1 | 96.5 | 96.1 | 96.5 | 95.4 |
| 10 mg | ** | 3.06 | 3.07 | | | 3.09 | 3.07 | 3.04 | 2.96 | 3.04 |
| TF/23077 | * | 100 | 102.1 | | | 101.6 | 97.5 | 96.6 | 95.0 | |
| 10 mg | ** | 2.81 | 2.81 | | | 2.74 | 2.65 | 2.67 | 2.75 | |
| TF/23078 | * | 100 | 98.3 | | | 97.7 | 96.5 | 95.9 | 98.8 | |
| 10 mg | ** | 3.50 | 3.59 | | | 3.47 | 2.27 | 3.43 | 3.51 | |
| TF/23117 | * | 100 | 95.7 | | | 95.8 | 97.8 | 96.2 | 95.5 | |
| 20 mg | ** | 2.97 | 2.97 | | | 2.92 | 2.85 | 2.96 | 2.98 | |
| TF/23119 | * | 100 | 97.6 | | | 97.8 | 96.2 | 97.3 | 96.8 | |
| 50 mg | ** | 3.08 | 2.94 | | | 2.94 | 2.87 | 2.99 | 3.00 | |
| H0001 | * | 100 | 98.2 | 99.4 | | 96.4 | 96.7 | | | |
| 10 mg | ** | 3.15 | 3.12 | 3.16 | | 3.05 | 3.23 | | | |
| L000 | * | 100 | 100.6 | 99.1 | | 98.1 | 98.3 | | | |
| 20 mg | ** | 3.05 | 2.84 | 2.83 | | 2.97 | 2.94 | | | |
| M0001 | * | 100 | 100.3 | 100.6 | | 98.7 | 99.0 | | | |
| 50 mg | ** | 3.20 | 2.96 | 2.97 | | 3.01 | 3.03 | | | |

* doxorubicin·HCl % stability
** pH

TABLE 22

Doxorubicin·HCl 2 mg/ml solution. Stability data at 15° C. (vials stored upright) acquired up to 12 months

| Batch Dosage | | 0 | 0.5 | 1 | 2 | 3 | 6 | 9 | 12 |
|---|---|---|---|---|---|---|---|---|---|
| TF/23049 | * | 100 | 97.8 | 98.9 | | 97.1 | 92.7 | 92.9 | 90.2 |
| 10 mg | ** | 3.06 | 3.03 | 3.07 | | 3.10 | 3.08 | 3.02 | 2.95 |
| TF/23077 | * | 100 | 100.4 | 101.9 | | 98.8 | 94.6 | 92.7 | 91.1 |
| 10 mg | ** | 2.81 | 2.81 | 2.85 | | 2.71 | 2.63 | 2.67 | 2.74 |
| TF/23078 | * | 100 | 101.4 | 98.4 | | 95.3 | 94.6 | 91.9 | 90.7 |
| 10 mg | ** | 3.50 | 3.51 | 3.58 | | 3.47 | 3.38 | 3.41 | 3.47 |
| TF/23117 | * | 100 | 99.1 | 96.4 | | 95.2 | 94.6 | 90.7 | |
| 20 mg | ** | 2.97 | 2.95 | 2.95 | | 2.90 | 2.81 | 2.95 | |
| TF/23119 | * | 100 | 97.4 | 97.1 | | 95.9 | 92.7 | 90.6 | |

TABLE 22-continued

Doxorubicin·HCl 2 mg/ml solution.
Stability data at 15° C. (vials stored upright)
acquired up to 12 months

| Batch | | Time (Months) | | | | | | | |
|---|---|---|---|---|---|---|---|---|---|
| Dosage | | 0 | 0.5 | 1 | 2 | 3 | 6 | 9 | 12 |
| 50 mg | ** | 3.08 | 2.99 | 2.95 | | 2.91 | 2.87 | 2.98 | |
| H0001 | * | 100 | | 97.9 | 97.1 | 94.8 | 94.6 | | |
| 10 mg | ** | 3.15 | | 3.12 | 3.16 | 3.06 | 3.23 | | |
| L000 | * | 100 | | 100.5 | 98.7 | 96.3 | 95.5 | | |
| 20 mg | ** | 3.05 | | 2.85 | 2.87 | 2.98 | 2.96 | | |
| M0001 | * | 100 | | 99.4 | 100.3 | 97.2 | 95.6 | | |
| 50 mg | ** | 3.20 | | 2.96 | 2.94 | 3.01 | 3.04 | | |

\* doxorubicin·HCl % stability
\*\* pH

TABLE 23

Doxorubicin·HCl 2 mg/ml solution. Stability data at 27° C. (vials stored upright) acquired up to 6 months.

| Batch | | Time (Months) | | | | | |
|---|---|---|---|---|---|---|---|
| Dosage | | 0 | 0.5 | 1 | 2 | 3 | 6 |
| TF/23049 | * | 100 | 97.2 | 95.8 | | 87.9 | 73.6 |
| 10 mg | ** | 3.06 | 2.98 | 3.07 | | 3.08 | 3.03 |
| TF/23077 | * | 100 | 98.5 | 96.2 | | 86.4 | 69.2 |
| 10 mg | ** | 2.81 | 2.80 | 2.85 | | 2.71 | 2.64 |
| TF/23078 | * | 100 | 101.2 | 94.5 | | 80.5 | 71.1 |
| 10 mg | ** | 3.50 | 3.51 | 3.58 | | 3.38 | 3.13 |
| TF/23117 | ** | 100 | 97.4 | 93.2 | | 81.9 | 66.6 |
| 20 mg | ** | 2.97 | 2.95 | 2.94 | | 2.88 | 2.77 |
| TF/23119 | * | 100 | 96.0 | 93.3 | | 85.3 | 66.8 |
| 50 mg | ** | 3.08 | 2.97 | 2.97 | | 2.91 | 2.82 |
| H0001 | * | 100 | | 94.5 | 94.2 | 86.6 | |
| 10 mg | ** | 3.15 | | 3.10 | 3.09 | 3.01 | |
| L000 | * | 100 | | 97.2 | 94.3 | 89.3 | |
| 20 mg | ** | 3.05 | | 2.84 | 2.85 | 2.96 | |
| M0001 | * | 100 | | 96.5 | 93.6 | 88.1 | |
| 50 mg | ** | 3.20 | | 2.95 | 2.95 | 2.99 | |

\* doxorubicin·HCl % stability
\*\* pH

TABLE 24

Doxorubicin·HCl 2 mg/ml solution. Stability data at 100 and 250 f.c. (vials stored inverted) acquired up to 3 months.

| Batch | Time | 100 foot-candles | | | | 250 foot-candles | | | |
|---|---|---|---|---|---|---|---|---|---|
| Dosage | Months | 0 | 0.5 | 1 | 3 | 0.5 | 1 | 2 | 3 |
| TF/23049 | * | 100 | 96.3 | 95.9 | 81.3 | 95.9 | 94.8 | | |
| 10 mg | ** | 3.06 | 3.05 | 3.05 | 3.06 | 2.99 | 3.04 | | |
| TF/23077 | * | 100 | 98.3 | 98.1 | 87.7 | 97.3 | 94.5 | | |
| 10 mg | ** | 2.81 | 2.79 | 2.84 | 2.70 | 2.79 | 2.84 | | |
| TF/23078 | * | 100 | 99.6 | 96.4 | 88.0 | 97.8 | 89.7 | | |
| 10 mg | ** | 3.50 | 3.50 | 3.58 | 3.39 | 3.47 | 3.53 | | |
| TF/23117 | * | 100 | 96.8 | 96.7 | 91.7 | 98.1 | 94.6 | | |
| 20 mg | ** | 2.97 | 2.93 | 2.95 | 2.87 | 2.9 | 2.93 | | |
| TF/23119 | * | 100 | 96.9 | 96.7 | 89.6 | 96.4 | 95.0 | | |
| 50 mg | ** | 3.08 | 2.96 | 2.95 | 2.93 | 2.96 | 2.97 | | |
| H0001 | * | 100 | | | | | 95.2 | 93.7 | 87.8 |
| 10 mg | ** | 3.15 | | | | | 3.10 | 3.06 | 2.97 |
| L000 | * | 100 | | | | | 96.5 | 93.0 | 86.5 |

TABLE 24-continued

Doxorubicin·HCl 2 mg/ml solution. Stability data at 100 and 250 f.c. (vials stored inverted) acquired up to 3 months.

| Batch | Time | 100 foot-candles | | | | 250 foot-candles | | |
|---|---|---|---|---|---|---|---|---|
| Dosage | Months | 0 | 0.5 | 1 | 3 | 0.5 | 1 | 2 | 3 |
| 20 mg | ** | 3.05 | | | | | 2.84 | 2.85 | 2.97 |
| M0001 | * | 100 | | | | | 97.8 | 91.5 | 85.3 |
| 50 mg | ** | 3.20 | | | | | 2.95 | 2.94 | 2.99 |

* doxorubicin·HCl % stability
** pH

TABLE 25

Stability studies. Batches tested.

| Batch | Batch No. | | |
|---|---|---|---|
| Characteristics | P0001 | Q0001 | R0001 |
| Doxorubicin·HCl per vial (mg) | 10 | 20 | 50 |
| pH | 3.00 | 3.00 | 3.00 |
| Formulation No. | FI6804/IL7 | FI6804/IL8 | FI6804/IL9 |
| Batch size No. of vials | 2,400 | 2,200 | 2,500 |

TABLE 26

Stability studies. Formulations tested.

| Composition per vial | Formulation number | | |
|---|---|---|---|
| | F16804/IL7 | F16804/IL8 | F16804/IL9 |
| Doxorubicin·HCl per vial (mg) | 10 | 20 | 50 |
| Hydrochloric acid q.s. to pH | 2.8–3.5 | 2.8–3.5 | 2.8–3.5 |
| 0.9% sodium chloride injection q.s. to ml | 5.0 | 10.0 | 25.0 |

TABLE 27

Stability studies. Packaging used.

| Packaging | Batch No. | | |
|---|---|---|---|
| | P0001 | Q0001 | R0001 |
| vial glass type | I | I | I |
| vial top capacity | 10 ml | 14 ml | 39 ml |
| stopper | chlorobutyl rubber, teflon-faced aluminum | chlorobutyl rubber, teflon-faced aluminum | chlorobutyl rubber, teflon-faced aluminum |
| seal | | | |

TABLE 28

Doxorubicin·HCl 2 mg/ml solution in Saline for Injection at pH = 3. Stability data at 4° C. (vials stored upright) acquired up to 9 and 12 months.

| Batch Dosage | | Time-Months | | | | |
|---|---|---|---|---|---|---|
| | | 0 | 3 | 6 | 9 | 12 |
| P0001 10 mg | doxorubicin·HCl % stability | 100 | 98.3 | 98.0 | 99.2 | |
| | pH | 3.00 | 2.93 | 2.98 | 2.90 | |
| Q0001 20 mg | doxorubicin·HCl % stability | 100 | 97.5 | 97.0 | 100.1 | |
| | pH | 3.01 | 3.06 | 3.03 | 3.00 | |
| R0002 50 mg | doxorubicin·HCl % stability | 100 | 99.8 | 100.7 | 101.2 | 101.7 |
| | pH | 3.02 | 3.08 | 3.15 | 3.14 | 3.10 |

TABLE 29

Doxorubicin·HCl 2 mg/ml solution in Saline for Injection at pH = 3. Stability data at 8° C. (vials stored upright) acquired up to 9 and 12 months

| Batch Dosage | | Time-Months | | | | | |
|---|---|---|---|---|---|---|---|
| | | 0 | 1 | 2 | 3 | 6 | 9 | 12 |
| P0001 10 mg | doxorubicin·HCl % stability | 100 | 101.0 | 100.6 | 97.9 | 97.4 | 96.8 | |
| | pH | 3.00 | 2.93 | 2.89 | 2.91 | 3.00 | 2.90 | |
| Q0001 | doxorubicin·HC % stability | 100 | 99.4 | 99.9 | 96.8 | 96.7 | 95.7 | |

TABLE 29-continued

Doxorubicin·HCl 2 mg/ml solution in Saline for Injection at pH = 3. Stability data at 8° C. (vials stored upright) acquired up to 9 and 12 months

| Batch Dosage | | Time-Months | | | | | | |
|---|---|---|---|---|---|---|---|---|
| | | 0 | 1 | 2 | 3 | 6 | 9 | 12 |
| 20 mg | pH | 3.01 | 3.02 | 3.01 | 3.05 | 3.02 | 3.00 | |
| | doxorubicin·HCl | | | | | | | |
| R0001 | % stability | 100 | 99.8 | 99.8 | 98.4 | 98.5 | 99.5 | 100.9 |
| 50 mg | pH | 3.02 | 3.02 | 3.09 | 3.08 | 3.13 | 3.13 | 3.10 |

TABLE 30

Doxorubicin·HCl 2 mg/ml solution in Saline for Injection at pH = 3 Stability data at 15° C. (vials stored upright) acquired up to 9 and 12 months.

| Batch Dosage | | Time-Months | | | | | | |
|---|---|---|---|---|---|---|---|---|
| | | 0 | 1 | 2 | 3 | 6 | 9 | 12 |
| P0001 | doxorubicin·HCl | | | | | | | |
| | % stability | 100 | 100.6 | 99.9 | 95.9 | 94.0 | 89.1 | |
| 10 mg | pH | 3.00 | 2.93 | 2.89 | 2.90 | 2.99 | 2.90 | |
| Q0001 | doxorubicin·HCl | | | | | | | |
| | % stability | 100 | 98.6 | 97.8 | 95.1 | 96.4 | 89.8 | |
| 20 mg | pH | 3.01 | 3.01 | 3.01 | 3.04 | 3.01 | 3.00 | |
| R0001 | doxorubicin·HCl | | | | | | | |
| | % stability | 100 | 98.8 | 97.5 | 97.6 | 94.7 | 96.0 | 94.5 |
| 50 mg | pH | 3.02 | 3.02 | 3.08 | 3.08 | 3.14 | 3.11 | 3.10 |

TABLE 31

Doxorubicin·HCl 2 mg/ml solution in Saline for Injection at pH = 3. Stability data at 27° C. (vials stored upright) acquired up to 3 months.

| Batch Dosage | | Time-Months | | | |
|---|---|---|---|---|---|
| | | 0 | 1 | 2 | 3 |
| P0001 | doxorubicin·HCl | | | | |
| | % stability | 100 | 98.3 | 95.0 | 84.9 |
| 10 mg | pH | 3.00 | 2.93 | 2.89 | 2.88 |
| Q0001 | doxorubicin·HCl | | | | |
| | % stability | 100 | 98.0 | 93.2 | 83.8 |
| 20 mg | pH | 3.01 | 3.01 | 2.99 | 3.03 |
| R0001 | doxorubicin·HCl | | | | |
| | % stability | 100 | 95.6 | 92.2 | 88.7 |
| 50 mg | pH | 3.02 | 3.02 | 3.06 | 3.05 |

TABLE 32

Doxorubicin·HCl 2 mg/ml solution in Saline for Injection at pH = 3. Stability data at R.T. +250 f.c. (vials stored upright) acquired up to 3 months.

| Batch Dosage | | Time-Months | | | |
|---|---|---|---|---|---|
| | | 0 | 1 | 2 | 3 |
| P0001 | doxorubicin·HCl | | | | |
| | % stability | 100 | 89.6 | 86.5 | 70.3 |
| 10 mg | pH | 3.00 | 2.92 | 2.86 | 2.84 |
| | doxorubicin·HCl | | | | |
| Q0001 | % stability | 100 | 91.1 | 84.5 | 72.7 |
| 20 mg | pH | 3.01 | 2.99 | 2.97 | 2.98 |
| | doxorubicin·HCl | | | | |
| R0001 | % stability | 100 | 96.0 | 91.4 | 86.6 |
| 50 mg | pH | 3.02 | 3.01 | 3.04 | 3.02 |

TABLE 33

Stability Data of Doxorubicin Solution, 2 mg/ml and a pH of 3.0 at 45° C.

| Stabilizing Agent and Its Concentration | % Initial | | | |
|---|---|---|---|---|
| | 1 Wk | 2 Wk | 4 Wk | 8 Wk |
| Water | 87.8 | 75.9 | 53.8 | 25.5 |
| 5% Dextrose | 91.1 | 82.3 | 65.6 | 38.8 |
| 5% Galactose | 91.5 | 86.1 | 64.3 | — |
| 5% Fructose | 91.9 | 80.6 | 64.1 | — |
| 4% α-L(−)-Fucose | 91.2 | 81.9 | 63.8 | — |
| 4% α-D(+)-Fucose | 91.8 | 81.9 | 63.3 | — |
| 1% Lactose | 91.3 | 81.7 | 64.5 | 34.8 |
| 4% Dextran, MW 9,000 | 90.5 | 81.5 | — | — |
| 4% Dextran, MW 506,000 | 92.0 | 84.0 | — | — |
| 4% α-Cyclodextrin | 91.7 | 84.3 | — | — |
| 4% β-Cyclodextrin | 92.1 | 84.1 | — | — |
| 4% γ-Cyclodextrin | 94.3 | 89.0 | — | — |

TABLE 33-continued

Stability Data of Doxorubicin Solution, 2 mg/ml and a pH of 3.0 at 45° C.

| Stabilizing Agent and Its Concentration | % Initial | | | |
|---|---|---|---|---|
| | 1 Wk | 2 Wk | 4 Wk | 8 Wk |
| 5% Mannitol | 90.7 | 81.4 | 65.8 | 41.1 |
| 5% Sorbitol | 91.4 | 83.0 | 67.2 | 42.5 |
| 0.5% Thioglycerol | 90.8 | 83.2 | 63.5 | — |
| 5% Inositol | 91.7 | 84.9 | — | — |
| 5% Ethanol | 92.2 | 85.6 | — | — |
| 10% Glycerol | 92.2 | 83.4 | 65.5 | — |

Note:
The same stabilizing effect may be seen for the above agents at lower concentrations, e.g., lower by up to 25–50 wt. %.

The invention now being fully described, it will be apparent to one of ordinary skill in the art that many changes and modifications can be made thereto without departing from the spirit or scope of the invention as set forth herein.

What is claimed as new and desired to be secured by Letters of Patent of the United States is:

1. A sealed glass container containing therein a stable, injectable, sterile, pyrogen-free doxorubicin anti-tumor composition in a solution which consists essentially of a physiologically acceptable salt of doxorubicin dissolved in a physiologically acceptable solvent therefore, wherein said solution has not been reconstituted from a lyophilizate, and wherein said solution has a pH of from 2.5–3.5 and a concentration of said doxorubicin of from 0.1 to 100 mg/ml.

2. A container, according to claim 1, wherein the pH of said solution is adjusted by addition of a physiologically acceptable acid which is selected from the group consisting of hydrochloric, hydrobromic, sulfuric, phosphoric, nitric, acetic, succinic, tartaric, ascorbic, citric, glutamic, benzoic, methanesulphonic, and ethansulphonic acid.

3. A container according to claim 1, wherein said container is hernmetically sealed.

4. A container according to claim 1, wherein the pH of said solution is from 2.7 to 3.5.

5. A container according to claim 1, wherein said solvent is a physiologically acceptable saline solution.

6. A container according to claim 1, wherein the pH of said solution is from 2.7up to 3.0.

7. A container according to claim 1, wherein said solvent is a physiologically acceptable dextrose solution.

8. A container according to claim 1, wherein said solvent is sterile water.

9. A container according to claim 1, wherein said physiologically acceptable salt of doxorubicin is selected from the group consisting of hydrochloric, hydrobromic, sulfuric, phosphoric, nitric, acetic, succinic, tartaric, ascorbic, citric, glutamic, benzoic, methanesulphonic, and ethanesulphonic acid salts.

10. A container according to claim 1, wherein the sterile, pyrogen-free physiologically acceptable solvent is selected from the group consisting of water, ethanol, polyethylene glycol, dimethylacetamide and mixtures thereof.

11. A container according to claim 1, which further contains a tonicity adjustment agent selected from the group consisting of sodium chloride, dextrose, lactose, mannitol, and sorbitol.

12. A container according to claim 11, containing about 0.9% w/v sodium chloride.

13. A container according to claim 11, containing about 5% w/v dextrose, lactose, mannitol or sorbitol.

14. A container according to claim 1, which further contains a preservative selected from the group consisting of esters of para-hydroxybenzoic acid and chlorocresol.

15. A container according to claim 1, wherein the concentration of doxorubicin is from 0.1 mg/ml to 50 mg/ml.

16. A container according to claim 1, wherein the concentration of doxorubicin is from 1 mg/ml to 20 mg/ml.

17. A container according to claim 1, wherein the rate constant of decomposition, measured under accelerated conditions at a temperature of around 55° C. and a concentration of said doxorubicin as the hydrochloride of around 2 mg/ml is less than about 0.150 day$^{-1}$.

* * * * *